US009592282B2

(12) United States Patent
Cohen et al.

(10) Patent No.: US 9,592,282 B2
(45) Date of Patent: *Mar. 14, 2017

(54) VACCINES FOR MALARIA

(75) Inventors: Joseph D. Cohen, Rixensart (BE); Martine Marchand, Rixensart (BE); Christian F. Ockenhouse, Silver Spring, MD (US); Anjali Yadava, Silver Spring, MD (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 1004 days.

This patent is subject to a terminal disclaimer.

(21) Appl. No.: 12/374,214

(22) PCT Filed: Jul. 16, 2007

(86) PCT No.: PCT/EP2007/057301
§ 371 (c)(1),
(2), (4) Date: Nov. 3, 2009

(87) PCT Pub. No.: WO2008/009652
PCT Pub. Date: Jan. 24, 2008

(65) Prior Publication Data
US 2010/0062028 A1   Mar. 11, 2010

(30) Foreign Application Priority Data

Jul. 18, 2006  (GB) .................................. 0614254.1
Jul. 20, 2006  (GB) .................................. 0614473.7
Jul. 20, 2006  (GB) .................................. 0614476.0
Jul. 28, 2006  (GB) .................................. 0615115.3

(51) Int. Cl.
*A61K 39/015*   (2006.01)
*A61K 39/00*    (2006.01)
*C07K 14/445*   (2006.01)
*C12N 7/00*     (2006.01)

(52) U.S. Cl.
CPC .......... *A61K 39/015* (2013.01); *C07K 14/445* (2013.01); *A61K 2039/6075* (2013.01); *C07K 2319/40* (2013.01)

(58) Field of Classification Search
None
See application file for complete search history.

(56) References Cited

U.S. PATENT DOCUMENTS

| 4,235,877 | A |   | 11/1980 | Fullerton, et al. |
| 4,912,094 | A |   | 3/1990  | Myers et al. |
| 4,997,647 | A |   | 3/1991  | Nussenzweig et al. |
| 5,278,302 | A |   | 1/1994  | Caruthers et al. |
| 5,554,372 | A | * | 9/1996  | Hunter ....................... 424/280.1 |
| 5,666,153 | A |   | 9/1997  | Copeland et al. |
| 6,083,716 | A |   | 7/2000  | Wilson et al. |
| 6,303,347 | B1 |  | 10/2001 | Johnson et al. |
| 6,544,518 | B1 |  | 4/2003  | Friede et al. |
| 6,558,670 | B1 |  | 5/2003  | Friede et al. |
| 6,660,498 | B1 | * | 12/2003 | Hui et al. ...................... 435/69.1 |
| 6,764,840 | B2 |  | 7/2004  | Johnson et al. |
| 7,790,186 | B2 | * | 9/2010  | Yadava et al. ............. 424/268.1 |
| 8,999,347 | B2 | * | 4/2015  | Cohen et al. .............. 424/185.1 |
| 9,364,525 | B2 | * | 6/2016  | Cohen .................. A61K 39/015 |
| 2003/0133944 | A1 |  | 7/2003 | Cohen |
| 2004/0067236 | A1 | * | 4/2004 | Cohen et al. .............. 424/185.1 |
| 2006/0041248 | A1 | * | 2/2006 | Patton et al. .............. 604/890.1 |
| 2006/0194196 | A1 |   | 8/2006 | Krupka et al. |
| 2008/0317787 | A1 | * | 12/2008 | Cohen ........................ 424/272.1 |
| 2010/0210004 | A1 | * | 8/2010 | Kappe et al. .............. 435/258.2 |

FOREIGN PATENT DOCUMENTS

| EP | 0 362 278     | 12/1988 |
| EP | 0 109 942     | 5/1989  |
| EP | 0 468 520     | 1/1992  |
| EP | 0 671 948 B1  | 8/1997  |
| EP | 0 689 454 B1  | 9/1997  |
| EP | 1 623 720 A   | 2/2006  |
| EP | 1 896 060 B1  | 12/2014 |
| GB | 2 220 211 A   | 1/1990  |

(Continued)

OTHER PUBLICATIONS

The New Riverside University Dictionary, The Riverside Publishing Company, p. 933, 1984.*
Illustrated Stedman's Medical Dictionary, 24th Edition, Williams and Wilkins, London, p. 707, 1982.*
New Riverside University Dictionary. The Riverside Publishing Company, p. 933, 1984.*
Illustrated Stedman's Medical Dictionary (24th Edition, Williams and Wilkins, London, p. 707, 1982.*
Venkatachalam, et al., "Immunogenicity of Plasmodium Falciparum and Plasmodium Vivax Circumsporozoite Protein Repeat Multiple Antigen Constructs (MAC)", *Vaccine*, 16:9-10, 982-988 (May 1998).
Thomas, et al., "Inducing a Cell-Mediated Immune Response Against Peptides of the Plasmodium Vivax Circumsporozoite Protein", *Annals of Tropical Medicine and Parasitology*, 95:6, 573-586 (Sep 2001).
Ballou, et al., "Safety and efficacy of a recombinant DNA plasmodium falciparum sporozoite vaccine" Lancet: i 1277 (1987).

(Continued)

*Primary Examiner* — S. Devi
(74) *Attorney, Agent, or Firm* — Virginia G. Campen

(57) ABSTRACT

The present invention relates to a novel hybrid/fusion protein derived from the CS protein of *Plasmodium vivax* (*P. vivax*), methods for preparing and purifying the same, its use in medicine, particularly in the prevention of malarial infections, for example those caused by *P. vivax*, compositions/vaccines containing the protein or antibodies against the protein such as monoclonal or polyclonal antibodies and use of the same, particularly in therapy. The invention also extends to lipoprotein particles of said hybrid protein and formulations/vaccines comprising the same and use thereof. In particular it relates to an immunogenic hybrid fusion protein comprising:
a. at least one repeat unit derived from the repeating region of a type I circumsporozoite protein of *P. vivax*,
b. at least one repeat unit derived from the repeating region of a type II circumsporozoite protein of *P. vivax*, and surface antigen S derived from Hepatitis B virus, or a fragment thereof.

27 Claims, 13 Drawing Sheets

(56) References Cited

FOREIGN PATENT DOCUMENTS

| | | |
|---|---|---|
| KR | 2000-0020497 | 4/2000 |
| WO | WO 93/10152 | 5/1993 |
| WO | WO 94/21292 | 9/1994 |
| WO | WO 95/26204 | 3/1995 |
| WO | WO 95/14026 | 5/1995 |
| WO | WO 95/17210 | 6/1995 |
| WO | WO 96/33739 | 10/1996 |
| WO | WO 98/05355 | 2/1998 |
| WO | WO 98/15287 | 4/1998 |
| WO | WO 98/50399 | 11/1998 |
| WO | WO 98/56414 | 12/1998 |
| WO | WO 01/46127 | 12/1999 |
| WO | WO 00/00462 | 1/2000 |
| WO | WO 02/13765 | 2/2002 |
| WO | WO 02/36792 | 5/2002 |
| WO | WO 03/000283 | 1/2003 |
| WO | WO 2004/037189 | 5/2004 |
| WO | WO 2004/055187 | 7/2004 |
| WO | WO 2004/113369 | 12/2004 |
| WO | WO 2005/001103 | 1/2005 |
| WO | WO 2005/025614 | 3/2005 |
| WO | WO 2006/029887 | 3/2006 |

OTHER PUBLICATIONS

Barr, et al; "Expression in Yeast of a Plasmodium Vivax Antigen of Potential Use in a Human Malaria Vaccine"; Journal Exp. Med.; vol. 165; 1160-1171 (1987).
Bett, et al., "Packaging capacity and stability of human adenovirus Type 5 vectors", J Virol 67 (10), 5911-21 (1993).
Broach, et al., "Transformation in Yeast Development of a Hybrid Cloning Vector and Isolation of the CAN 1 Gene", Gene 8: 121-133, (1979).
Clyde, "Immunization of man against falciparum and vivax malaria by uses of attenuated sporozoites", Am. J, Trop. Med. Hyg 24: 397-402, (1975).
Collins, et al., "Immunization of *Saimiri Sciureus Boliviensis* with recombinant vaccines based on the circumsporozoite protein of *Plasmodium Vivax*", Am. J. Trop. Med. Hyg. 40, 455-64 (1989).
Dalsgaard et al. in 1974 ("Saponin adjuvants", Archiv. für die gesamte Virusforschung, vol. 44, Springer Verlag, Berlin, 243-254).
Dame, et al., "Structure of the Gene Encoding the Immunodominant Surface Antigen on the Sporozoites of the Human Malaria Parasite Plasmodium falciparum", Science 225: 593-599, (1984).
Fitzgerald, et al., "A Simian Replication-Defective Adenoviral Recombinant Vaccine to HIV-1 Gag", J. Immunol. 170:1416 (2003).
Gantt, et al; "Cell Adhesion to a Motif Shared by the Malaria Circumsporozoite Protein and Thrombospondin Is Mediated by Its Glycosaminoglycan-binding Region and Not by CSVTCG"; The Journal of Biological Chemistry; 1997; vol. 272, No. 31; 19205-19213; The American Society for Biochemistry and Molecular Biology Inc.
Harford, et al., "Construction and Characterization of a *Saccharomyces cerevisiae* Strain (RIT4376) Expressing Hepatitis B Surface Antigen", *Postgrad* Med J 63, Supp. 2: 65-70, (1987).
Heppner. et al., Towards an RTS,S-based, multi-stage, multi-antigen vaccine against falciparum malaria: progress at the Walter Reed Army Institute of Research, Vaccine 23, 2243-50 (2005).

Herrington, et al., "Safety and immunogenicity in man of a synthetic peptide malaria vaccine against *Plasmodium falciparum sporozoites*", Nature 328:257 (1987).
Hinnen , et al., "Transformation of Yeast", Proc Natl Acad Sci USA 75: 1929-1933, (1978).
Jacobs, et al., "Simultaneous Synthesis and Assembly of Various Hepatitis B Surface Proteins in *Saccharomyces cerevisiae*", Gene 80: 279-291, (1989).
Nardelli, et al., "The MAP System: A flexible and unambiguous vaccine design of branched peptides", Pharm. Biotechnol. 6, 803-19. (1995).
Parks, et al., "A Helper-Dependent System for Adenovirus Vector Production Helps Define a Lower Limit for Efficient DNA Packaging", J Virol 71(4), 3293-8 (1997).
Qari, et al., Wide distribution of the variant form of the human malaria parasite *plasmodium vivax*, JournalOfBiolChem 266(25):16297-16300 (1991).
Rathore, et al., "Binding and Invasion of Liver Cells by Plasmodium falciparum Sporozoites", J. Biol. Chem. 277(9): 7092-7098, (2002).
Roy et al., "Characterization of a Family of Chimpanzee Adenoviruses and Development of Molecular Clones for Gene Transfer Vectors" Human Gene Therapy 15:519-530 (2004).
Russell W.C., "Update on adenovirus and its vectors", Gen Viriol, 81:2573-2604 (2000).
Suh, et al., "Comparison of Immunological Responses to Various Types of Circumsporozoite Proteins of Plasmodium vivax in Malaria Patients of Korea", Microbiol. Immunol. 48(2): 119-123, Microbiol. Immunol. 2004; 48(2): 119-123 (2004).
Valenzuela, et al., "Nucleotide sequence of the gene coding for the major protein of hepatitis B virus surface antigen", Nature 280:815-819 (1979).
Vieira, et al., "The pUC plasmids, an M13mp7-Derived System for Insertion Mutagenesis and Sequencing with Synthetic Universal Primers", Gene 19: 259-268, (1982).
Zhang, et al., "Double Stranded DNA Sequencing as a Choice for DNA Sequencing", Nucleic Acids Research 16: 1220, (1988).
Pages 65-70 of Evidence 1 as Common Knowledge; "High-tech approaches to the control of infections diseases", 1996; ISBN 7534520452 (CN Patent Application No. 200780034644.0).
Chitnis, et al., "Targeting the Plasmodium vivax Duffy-binding protein", Trends in Parasitology, 24(1):29-34 (2007).
Martinez, et al., "Plasmodium vivax Duffy binding protein: a modular revolutionary proposal" Parasitology, 128, 353-366 (2004).
Miller, "Erythrocyte receptors for (Plasmodium knowlesi) Malaria: Duffy blood group determinants", Science, 189(4202):561-563 (1975).
Schodel, et al., "Hybrid hepatitis B virus core antigen as a vaccine carrier moiety: I. Presentation of foreign epitopes", Journal of Biotechnology, 44:91-96 (1996).
Sun, et al., "Protective Immunity Induced with Malaria Vaccine, RTS,S, Is Linked to *Plasmodium falciparum* Circumsporozoite Protein-Specific CD4+ and CD8+ T Cells Producing IFNγ1", *The Journal of Immunology*, 171: 6961-6967 (2003).
Thomas, et al., "Inducing a Cell-Mediated Immune Response Against Peptides of the Plasmodium Vivax Circumsporozoite Protein", *Annals of Tropical Medicine and Parasitology*, 95:6, 573-586 (Sep. 2001).

* cited by examiner

FIG 1 Electron micrograph of CSV-S particles produced in strain Y1834

4-20% "Cambrex"type minigel
15ul clarified extract / lane (+/- 50ug

1: DC5 host strain (negative control)
2: Y1834 (CSV-S)
3: Y1631 ( RTS,S)

FIG 2B

1) DC5 host strain (negative control)

2) Y1834 (CSV- S)
3) clone #2 (CSV-S)
4) clone #3 (CSV-S)
5) clone #1 (CSVtr-S)
6) clone #2 (CSVtr-S)
7) clone #3 (CSVtr-S)

Plasmid map of pRIT15546

ATG ATG GCT CCC GGG ATC CTA CCC GGG CCT GTG ACG AAG ATG ...
 M   M   A   P    G   I   L   P    G   P   V   T   N   M
          SmaI            SmaI
                                      préS2          S

Figure 5: Plasmid map of pRIT 15607
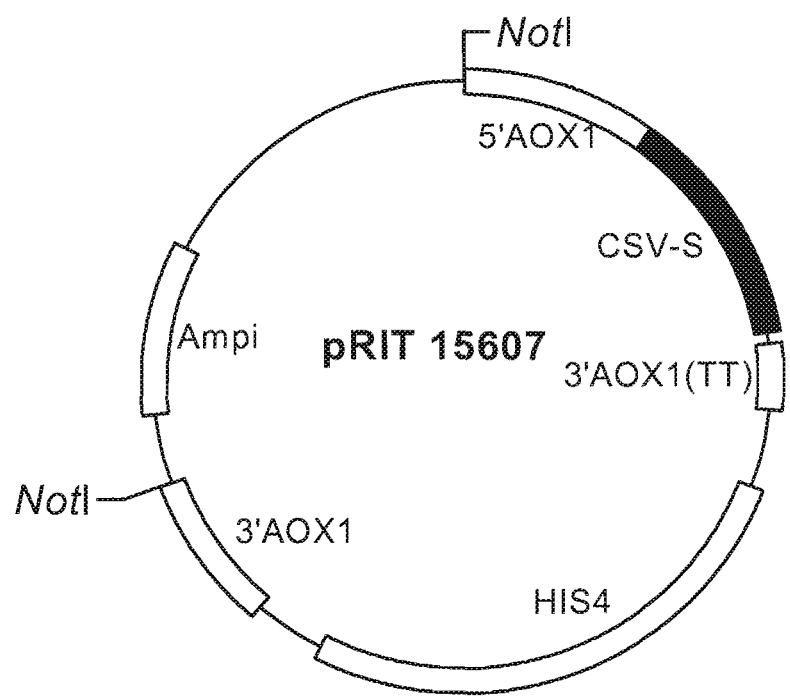

Figure 6: Western blot of recombinant protein expressed in strain Y1840

WB revealed with anti-S antibody
Quantity of total protein loaded is in brackets.

1: GS115 (*Pichia pastoris* host cell)
2: Y1840 (100µg)
3: Y1840 (50µg)
4: Y1840 (25µg)
5: Y1840 (12.5µg)
6: Y1833 (100µg, S.c. strain expressing CSV-S)
7: Y1835 (100µg, S.c. strain co-expressing CSV-S and S )

Figure 7: Electron micrograph of CSV-S particles produced in strain Y1840

Figure 8: Plasmid map of pRIT15582.
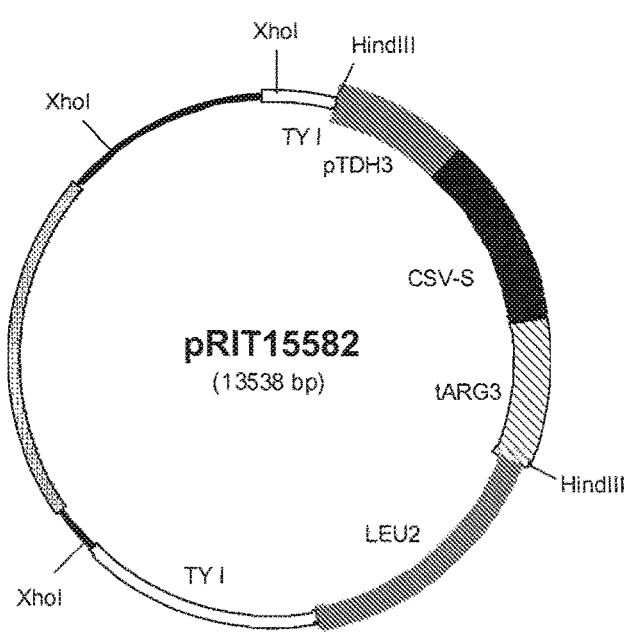

Figure 9: Restriction map of the linear XhoI fragment used to integrate CSV-S cassette.

Figure 10: Western blot of recombinant proteins expressed in strain Y1835.

Figure 11: Electron micrograph of CSV-S,S mixed particles produced in strain Y1835

Figure 12
(Seq Id No 21)

```
                  *        20         *        40         *        60         *
CSV-S   : MMAPGTHCGHNVDLSKAINLNGVNFNNVDASSLGAAHVGQSASRGRGLGENPDDEEGDAKKKKDGKKAEPKNPRENKL :
78
CSVtr-S : MMAP--------------------------------------------------------------AEPKNPRENKL :
15

80         *       100         *       120         *       140         *
CSV-S   : KQPGDRADGQAAGNGAGGQPAGDRAAGQPAGDRAAGQPAGDGAAGQPAGDRADGQPAGDRADGQPAGDRAAGQAAGNG :
156
CSVtr-S : KQPGDRADGQAAGNGAGGQPAGDRAAGQPAGDRAAGQPAGDGAAGQPAGDRADGQPAGDRADGQPAGDRAAGQAAGNG :
93

160         *       180         *       200         *       220         *
CSV-S   : AGGQAAANGAGNQPGGGNAANKKAEDAGGNAGGNAGGQGQNNEGANAPNEKSVKEYLDKVRATVGTEWTPCSVTCGVG :
234
CSVtr-S : AGGQAAANGAGNQPGGGNAANKKAEDAGGNAGGNAGGQGQNNEGANAPNEKSVKEYLDKVRATVGTEWTPCSVTCGVG :
171

240         *       260         *       280         *       300         *
CSV-S   : VRVRRRVNAANKKPEDLTLNDLETDVCTPGPVTNMENITSGFLGPLLVLQAGFFLLTRILTIPQSLDSWWTSLNFLGG :
312
CSVtr-S : VRVRRRVNAANKKPEDLTLNDLETDVCT-GPVTNMENITSGFLGPLLVLQAGFFLLTRILTIPQSLDSWWTSLNFLGG :
248

320         *       340         *       360         *       380         *
CSV-S   : SPVCLGQNSQSPTSNHSPTSCPPICPGYRWMCLRRFIIFLFILLLCLIFLLVLLDYQGMLPVCPLIPGSTTTNTGPCK :
390
CSVtr-S : SPVCLGQNSQSPTSNHSPTSCPPICPGYRWMCLRRFIIFLFILLLCLIFLLVLLDYQGMLPVCPLIPGSTTTNTGPCK :
326

400         *       420         *       440         *       460         *
CSV-S   : TCTTPAQGNSMFPSCCCTKPTDGNCTCIPIPSSWAFAKYLWEWASVRFSWLSLLVPFVQWFVGLSPTVWLSAIWMMWY :
468
CSVtr-S : TCTTPAQGNSMFPSCCCTKPTDGNCTCIPIPSSWAFAKYLWEWASVRFSWLSLLVPFVQWFVGLSPTVWLSAIWMMWY :
404

*       480         *
CSV-S   : WGPSLYSIVSPFIPLLPIFFCLWVYI- : 494
CSVtr-S : WGPSLYSIVSPFIPLLPIFFCLWVYI- : 430
```

VACCINES FOR MALARIA

This application is a 371 of International Application No. PCT/EP2007/057301, filed Jul. 16, 2007, which is incorporated herein by reference in its entirety. This application also claims benefit of the earlier filing dates of GB Applications No. 0614254.1, filed Jul. 18, 2006, 0614473.7, filed Jul. 20, 2006, 0614476.0, filed Jul. 20, 2006, and 0615115.3 filed Jul. 28, 2006.

Aspects of the invention described herein are subject to a joint research agreement between Walter Reed Army Institute of Research of the United States Army and GlaxoSmithKline Biologicals, s.a.

The present invention relates to a novel hybrid/fusion protein, methods for preparing and purifying the same, its use in medicine, particularly in the prevention of malarial infections, for example those caused by *Plasmodium vivax* (*P. vivax*), compositions/vaccines containing the protein or antibodies against the protein such as monoclonal or polyclonal antibodies and use of the same, particularly in therapy. The invention also extends to lipoprotein particles of said hybrid/fusion protein and formulations/vaccines comprising the same and use thereof.

Malaria is one of the world's major health problems with more than 2 to 4 million people dying from the disease each year. One of the most prevalent forms of the disease is caused by the protozoan parasite *P. vivax*, which is found in tropical and sub-tropical regions. Interestingly the parasite can complete its mosquito cycle at temperatures as low as 15 degrees Celsius, which has allowed the disease to spread in temperate climates.

The life cycle of *P. vivax* is complex, requiring two hosts, man and mosquito for completion. The infection of man is initiated by the introduction of sporozoites in the saliva of an infected mosquito. The sporozoites migrate to the liver and there infect hepatocytes where they differentiate, via the exoerythrocytic intracellular stage, into the merozoite stage which infects red blood cells (RBC) to initiate cyclical replication in the asexual blood stage. The cycle is completed by the differentiation of a number of merozoites in the RBC into sexual stage gametocytes which are ingested by the mosquito, where they develop through a series of stages in the midgut to produce sporozoites which migrate to the salivary gland.

Due to the fact that the disease caused by *P. vivax* is rarely lethal, efforts to prevent and treat malaria have been focused on the more deadly form of the disease caused by *Plasmodium falciparum* (*P. falciparum*).

Although the disease caused by *P. vivax* does not usually result in death of the patient, due to the volume of cases, which seems to be increasing, the significant impact on the quality of life of the patient, the increasing reports of the severe incidences of the disease resulting in anemia and death, and the economic impact, an effective vaccination for the disease is still required.

A feature of the *P. vivax* is that some strains are capable of causing delayed infection by remaining latent in the liver before emerging into the peripheral circulation to manifest clinical symptoms. Thus individuals, for example when traveling through an infected area, may be infected and yet may not exhibit symptoms for several months. This has the potential to cause the spread of the disease and for this reason persons traveling to infected areas are not allowed to donate blood for transfusion for a defined period of time after traveling to the infected region.

*P. vivax* malaria infection remains latent within the liver while the parasite is undergoing pre-erthrocytic shizogony. If the parasite is controlled at this stage before it escapes the liver no clinical symptoms of the disease, are observed in the patient.

The sporozoite stage of *P. vivax* has been identified as a potential target of a malaria vaccine. Vaccination with deactivated (irradiated) sporozoite has been shown to induce protection against experimental human malaria (Am. J, Trop. Med. Hyg 24: 297-402, 1975). However, it is has not been possible practically and logistically to manufacture a vaccine for malaria for the general population based on this methodology, employing irradiated sporozoites.

The major surface protein of the sporozoite is known as circumsporozoite protein (CS protein). It is thought to be involved in the motility and invasion of the sporozoite during its passage from the initial site of inoculation by the mosquito into the circulation, where it migrates to the liver.

The CS protein of Plasmodia species is characterized by a central repetitive domain (repeat region) flanked by non-repetitive amino (N-terminus) and carboxy (C-terminus) fragments. The central domain of *P. vivax* is composed of several blocks of a repeat unit, generally of nine tandem amino acids.

In certain Asian strains, after the central repeat region, an additional sequence of approximately 12 amino acids is present (see SEQ ID NO: 11). The function of the latter is not known. However, it is hypothesized by some that said amino acids may be linked to the delayed onset of clinical symptoms of the disease, although this has not been investigated. It is thought that the N-terminus is characterised by a sequence of 5 amino acids known as region I (see SEQ ID NO: 1). It is also thought that the C-terminus is characterised by comprising a sequence of 18 amino acids known as region II. The latter contains a cell-adhesive motif, which is highly conserved among all malaria CS protein (see SEQ ID NO: 2).

Several groups have proposed subunit vaccines based on the circumsporozoite protein. Two of these vaccines have undergone clinical testing; one is a synthetic peptide, the other is a recombinant protein (Ballou et al Lancet: i 1277 (1987) and Herrington et al Nature 328:257 (1987)). These vaccines were successful in stimulating an anti-sporozoite response. Nonetheless, the magnitude of the response was disappointing, with some vaccinees not making a response at all. Furthermore, the absence of "boosting" of antibody levels on subsequent injections and results of in vitro lymphocyte proliferation assays suggested that T-cells of most of these volunteers did not recognise the immunodominant repeat. Nonetheless, one volunteer vaccinated in each study did not develop parasitemia.

WO 93/10152 and WO 98/05355 describe a vaccine derived from the CS protein of *P. falciparum* and it seems that there has been some progress made towards the vaccination against *P. falciparum* using the approach described therein, see also Heppner et al. 2005, Vaccine 23, 2243-50.

The CS protein in *P. falciparum* has a central repeat region that is conserved. In contrast at least two forms (designated VK210 or type I and VK247 or type II) of the CS protein for *P. vivax* are known. This renders it more difficult to identify a construct of the CS protein with all the desired properties such as immogenicity, which provides general protection against *P. vivax* regardless of the specific type of CS protein because antibodies directed the central repeating region of type I do not necessarily recognize epitopes on the corresponding region of type II and vice versa.

A recombinant *P. vivax* CS protein was expressed and tested as a vaccine in the 1980-1990's with limited success (Collins et al., 1989. Am. J. Trop. Med. Hyg. 40, 455-64).

Some work has been done to develop a vaccine based on Multiple Antigen Peptides (MAP) employing one or more epitopes that are cross-linked (Nardelli and Tam, 1995, Pharm. Biotechnol. 6, 803-19).

The present invention provides a new, improved antigen for use in malaria vaccines, which is believed to produce a humoral response and also a cellular immune response. The antigen/particle is believed to induce the production of antibodies against the CS protein of type I and type II. The antigen/particle may also induce T helper cells for example Th1 and/or Th2 cells.

Accordingly, the present invention provides an immunogenic hybrid fusion protein comprising:
a. at least one repeat unit derived from the central repeat section of a type I circumsporozoite protein of *P. vivax*,
b. at least one repeat unit derived from the central repeating section of a type II circumsporozoite protein of *P. vivax*, and
c. surface antigen S derived from Hepatitis B virus.

SEQUENCE LISTING

SEQ ID NO: 1 Region I in the N-terminus (described above)
SEQ ID NO: 2 Motif from Region II in the C-terminus (described above)
SEQ ID NOs: 3-9 Various monomers of type I CS protein
SEQ ID NO: 10 Major monomer from type II CS protein
SEQ ID NO: 11 Additional amino acids found in Asian strains
SEQ ID NO: 12 Nucleotide sequence for the hybrid protein (optimized for expression in *E Coli*)
SEQ ID NO: 13 Amino acid sequence for the hybrid protein CSV
SEQ ID NO: 14 Minor monomer from type II CS protein
SEQ ID NO: 15 Nucleotide sequence for the hybrid protein CSV (optimized for expression in yeast)
SEQ ID NO: 16 Nucleotide sequence for the hybrid fusion protein CSV-S
SEQ ID NO: 17 Amino acid sequence for the hybrid fusion protein CSV-S
SEQ ID NO: 18 Nucleotide sequence for an RTS expression cassette and predicted RTS,S protein.
SEQ ID NO: 19 Nucleotide sequence for the hybrid fusion gene CSV-S (cloned into pHIL-D2 integrative *Pichia pastoris* expression vector)
SEQ ID NO: 20 Amino acid sequence for the hybrid fusion protein CSV-S expressed in *Pichia pastoris*
SEQ ID NO: 21 Shown in FIG. 12 is a comparison of the sequence of a full length recombinant CSV-S protein (SEQ ID NO:17) and a truncated protein (CSVtr-S) (SEQ ID NO:30).
SEQ ID NO: 22 Cloning site of plasmid pGF1-S2
SEQ ID NO: 23 Peptide sequence encoded by cloning site of plasmid pGF1-S2
SEQ ID NOs: 24-29 Example of CpG oligonucleotides. 1
SEQ ID NO: 30 Example of a truncated version of the CS protein (CSVtr-S).

FIGURES

FIG. 1 Shows an electron micrograph of multimer lipoprotein particles of the hybrid protein of the invention produced in yeast strain *S. cerevisiae* (with a constitutive promoter)

Figure 2A:
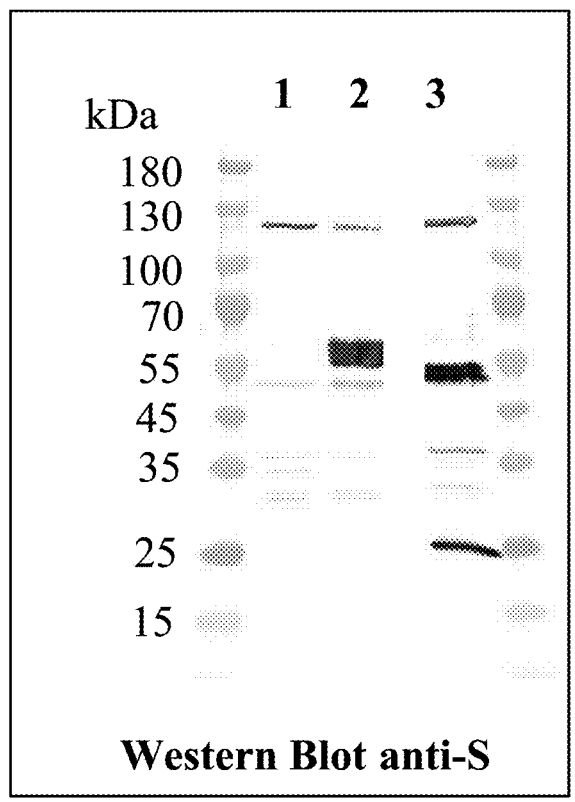
FIG. 2A Is a Western Blot of a hybrid protein of the invention and comparator proteins (part of gel)

FIG. 2B Is a Western Blot of a hybrid protein of the invention and comparator proteins (full gel of FIG. 2A, wherein lanes 1, 2 and 3 in FIG. 2A are lanes 1, 2 and 8 in FIG. 2B)

Figure 3:
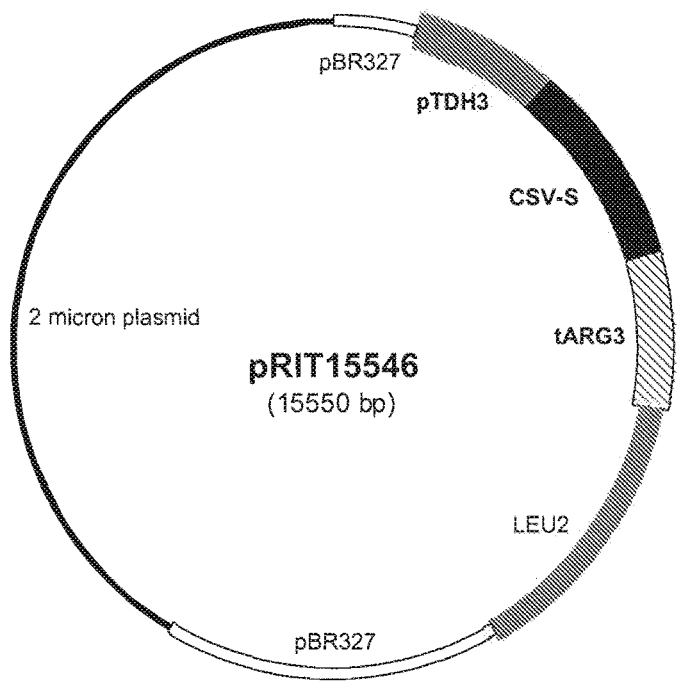

FIG. 3 Plasmid map for pRIT15546 recombinant vector employed for introducing the sequence encoding for the CSV-S fusion protein into the yeast host cell (episomal vector).

Figure 4:
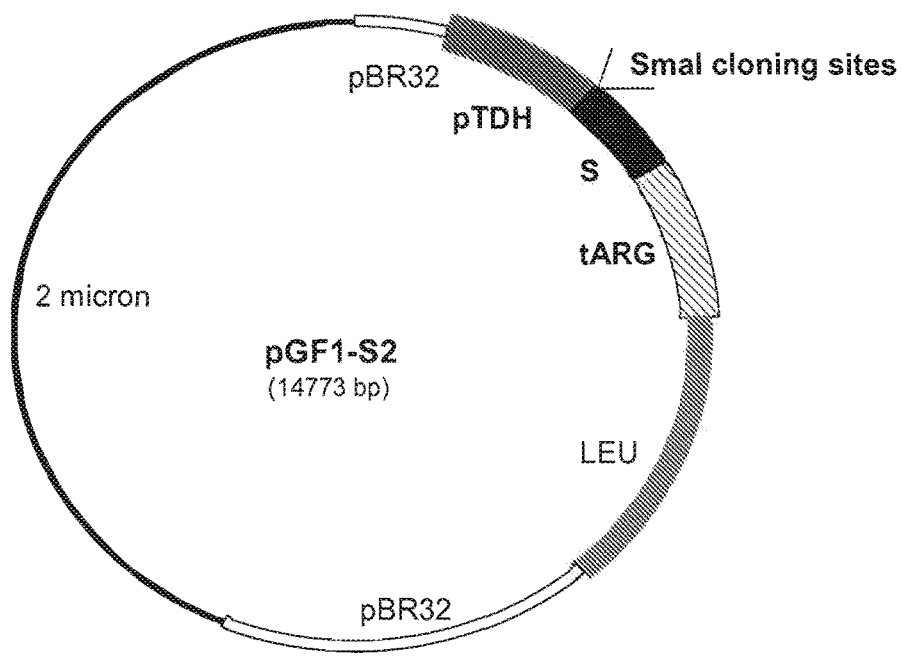

FIG. 4 Plasmid map of pGF1-S2 a plasmid prepared by GSK employed in forming the fusion protein of a desired antigen with the S antigen from Hepatitis B. [SEQ ID NO: 22]
Cloning heterologous DNA sequences between SmaI sites (after excision of the 12 bp SmaI DNA fragment) creates in-frame fusion with the S gene. [SEQ ID NO: 23]

FIG. 5 Plasmid map of Prit 15607 employed in forming the fusion protein of a desired antigen with the S antigen from Hepatitis B Digestion with NotI liberates a 6.8 kb linear DNA fragment carrying the CSV-S expression cassette plus the HIS4 selective marker, being used for insertion into the yeast chromosome.

FIG. 6 Shows a Western Blot of recombinant protein expressed in Y1840

FIG. 7 Shows an electron micrograph of multimer lipoprotein particles of the hybrid protein of the invention produced in *Pichia pastoris* (a "non-conventional" yeast, a methylotrophic yeast, in which the recombinant expression is driven by a methanol inducible promoter).
CSV-S particles were purified from soluble extracts (based on RTS,S purification process) and submitted to electron microscopy analysis. Particles were visualized after negative staining with phosphotungstic acid. The scale is equivalent to 100 nm.

FIG. 8 Plasmid map of pRIT15582
Digestion with XhoI liberates a 8.5 kb linear DNA fragment carrying the CSV-S expression cassette plus the LEU2 selective marker, being used for insertion into the yeast chromosome.

FIG. 9 Restriction map of the linear XhoI fragment used to integrate CSV-S cassette FIG. 10 Western blot of recombinant proteins expressed in strain Y1835.
Panel A: WB revealed with anti-S antibody
Samples loaded (100 µg total protein/well):
1: Y1631 (RTS,S producing strain, as comparison)
2: Y1835
3: Y1835
4: Y1834
Panel B: WB revealed with anti-CSV antibody
Samples loaded (100 µg total protein/well):
1: Y1631 (RTS,S producing strain, as comparison)
2: Y1295
3: Y1835
4: Y1834
5: nr (another construct CSVS)
6: nr (another construct –S antigen only)

FIG. 11 Electron micrograph of CSV-S,S mixed particles produced in strain Y1835
CSV-S,S particles were purified from soluble cell extracts (based on RTS,S purification process) and submitted to electron microscopy analysis. Particles were visualized after negative staining with phosphotungstic acid. The scale is equivalent to 100 nm.

FIG. 12 Shows a comparison of recombinant full length CS protein [SEQ ID NO: 17] and a truncated version of the CS protein (CSVtr-S) [SEQ ID NO: 30].

Hybrid protein herein refers to protein derived from *P. vivax* type I and type II.

Hybrid fusion protein herein refers to protein derived from *P. vivax* type I and type II fused to another protein or fragment thereof In one aspect the hybrid fusion protein of the invention comprises a hybrid protein derived from the CS proteins of *P. vivax* (CSV) and a surface antigen from Hepatitis B, generally the major surface protein known as the S antigen, such as the S antigen derived from an adw serotype.

The CSV derived antigen component (ie the hybrid protein) of the invention is generally fused to the amino terminal end of the S protein. More specifically the C-terminus end of the CSV fragment is fused the N-terminus of said S antigen.

It is believed that the presence of the surface antigen from Hepatitis B boosts the immunogenicity of the CS protein portion of the hybrid protein, aids stability, and/or assists reproducible manufacturing of the protein.

Generally the hybrid protein will also contain an N-terminus fragment from a CS protein of *Plasmodium* such as *P. vivax* (type I or II), for example a fragment comprising region I such as the amino acids shown in SEQ ID NO:1.

Alternatively the hybrid protein may contain an N-terminus fragment from the CS protein of *P. falciparum*.

In one aspect the hybrid protein may comprise one or more repeat units from the central region of *P. falciparum*. For example 1, 2, 3, 4, 5, 6, 7, 8, 9 or more repeat units.

Usually the hybrid protein will contain a C-terminus fragment from a CS protein of *Plasmodium* such as *P. vivax* (type I or II), for example a fragment comprising region II such as shown in SEQ ID NO: 2.

Alternatively the hybrid protein may contain a C-terminus fragment from the CS protein of *P. falciparum*.

Whilst not wishing to be bound by theory it is thought that the N and C terminal fragments include several T and B cell epitopes.

In recombinant proteins often unnatural amino acids are introduced in the cloning process and are observed in the final expressed protein. For example several such as 1, 2, 3, 4 or 5 amino acids may be inserted at the beginning (N-terminal) of the protein. If 4 amino acids are inserted at the beginning of the protein they may for example be MMAP. In addition to or alternatively 1, 2, or 3 such as 1 amino acids may be inserted into the body/middle of the protein at for example about amino acid, 259, 260, 261 or 262. The amino acid insert may be the amino acid with the symbol P. In one aspect the protein employed does not include any amino acids inserted by the cloning process in the body/middle of the protein.

The invention also extends to a so-called "truncated" version of the hybrid protein, for example as shown in FIG. 12 and labeled CSVtr-S.

Thus the invention provides truncated hybrid protein wherein at least the arginine rich region found in the N-terminal of the CS protein (about amino acid 60) is removed/deleted.

In one aspect the invention provides a truncated hybrid protein, wherein at least amino acids 1 to 55 (or 1 to 56, 57, 58, 59, 60, 61, 62, 63, 64, 65, 66, 67, 68, 69 or 70) is deleted. This truncated hybrid protein may include up to 4 amino acids inserted at the beginning of the protein such as MMAP.

In one aspect the invention relates to a hybrid proteins, which excludes amino 5 to 64 (inclusive) of the full length recombinant protein.

This/these truncated hybrid protein may be employed in other aspects of the invention described below.

Any suitable strain of *P. vivax* may be employed in the invention including: Latin America/South America (ie Sal 1, Belem), Korea, China, Thailand, Indonesia, India, and Vietnam. The construct in SEQ ID NO: 13 is based on a Korean strain (more specifically a South Korean strain).

*P. vivax* with type I CS proteins is more prevalent than *P. vivax* with type II CS proteins. Therefore in one aspect of the invention more repeat units from type I are included in the hybrid than repeat units of type II.

More specifically the hybrid protein of the invention may include 1 to 15 repeat units such as 9 repeat units from type I.

Examples of suitable monomers of type I CS proteins are given in SEQ ID NOs: 3 to 9.

In one embodiment the invention provides a hybrid protein comprising a mixture of different repeat units of type I, such as one of each of those listed in SEQ ID NOs: 3 to 9.

One or more repeat units may be duplicated in the hybrid, for example two monomers of SEQ ID NO: 3 and/or 4 may be incorporated into the construct.

a) In one aspect the CS protein comprises a unit of SEQ ID NO: 3.

b) In one aspect the CS protein comprises a unit of SEQ ID NO: 4, optionally in combination with a unit as described in paragraph a) directly above.

c) In one aspect the CS protein comprises a unit of SEQ ID NO: 5, optionally in combination with a unit as described in paragraph a) or b) directly above.

d) In one aspect the CS protein comprises a unit of SEQ ID NO: 6, optionally in combination with one or more units as described in paragraphs a) to c) directly above.

f) In one aspect the CS protein comprises a unit of SEQ ID NO: 7, optionally in combination with one or more units as described in paragraph a) to d) directly above.

g) In one aspect the CS protein comprises a unit of SEQ ID NO: 8, optionally in combination with one or more units as described in paragraph a) to f) directly above.

h) In one aspect the CS protein comprises a unit of SEQ ID NO: 9, optionally in combination with one or more units as described in paragraph a) to g) directly above.

Examples of suitable component repeat units of type II CS proteins are given in SEQ ID NOs: 10 and 14, such as 10.

In one aspect of the invention there is provided a hybrid protein with 5 or less repeat units derived from type II such as one monomer, for example as shown in SEQ ID NO: 10.

The hybrid protein may also include the 12 amino acid insertion found at the end of the repeat region found in certain Asian strains of *P. vivax*, for example as shown in SEQ ID NO: 11.

In one embodiment the hybrid protein comprises 257 amino-acids derived from *P. vivax* CS protein.

In one embodiment the hybrid fusion protein comprises 494 amino acids, for example 257 of which are derived from *P. vivax* CS protein.

In one aspect the CS protein comprises full length protein.

In one aspect the CS protein employed is a truncated version, for example as shown in FIG. 12 or a corresponding truncated wherein the amino acids about 1 to about 67 are deleted.

In one embodiment between 1 and 5 additional amino acids are inserted at the beginning of the sequence as a result of the cloning process, for example MMAP or MMAPG inserted.

The hybrid protein and/or fusion protein may also include further antigens derived from *P. falciparium* and/or *P. vivax*, for example wherein the antigen is selected from DBP, PvTRAP, PvMSP2, PvMSP4, PvMSP5, PvMSP6, PvMSP7, PvMSP8, PvMSP9, PvAMA1 and RBP or a fragment thereof.

In an embodiment the hybrid fusion protein (CSV-S) has substantially the amino acid sequence shown in SEQ ID NO: 17. In the sequence, amino acids 6 to 262 are derived from CSV and 269 to 494 are derived from S. The remaining amino acids are introduced by genetic construction (these may, in particular, be varied if desired).

The properties of the CSV-S fusion protein of SEQ ID NO: 17 are provided in the Tables below:

| Analysis | Whole Protein |
| --- | --- |
| Molecular Weight | 51794.75 m.w. |
| Length | 494 |
| 1 microgram = | 19.307 pMoles |
| Molar Extinction coefficient | 90780 +/− 5% |
| 1 A(280) = | 0.57 mg/ml |
| Isoelectric Point | 7.33 |
| Charge at pH 7 | 1.05 |

Whole Protein Composition Analysis

| Amino Acid(s) | Number count | % by weight | % by frequency |
| --- | --- | --- | --- |
| Charged (RKHYCDE) | 106 | 26.35 | 21.46 |
| Acidic (DE) | 38 | 8.82 | 7.69 |
| Basic (KR) | 39 | 10.68 | 7.89 |
| Polar (NCQSTY) | 134 | 28.15 | 27.13 |
| Hydrophobic (AILFWV) | 167 | 34.68 | 33.81 |
| A Ala | 52 | 7.14 | 10.53 |
| C Cys | 18 | 3.58 | 3.64 |
| D Asp | 24 | 5.33 | 4.86 |
| E Glu | 14 | 3.49 | 2.83 |
| F Phe | 17 | 4.83 | 3.44 |
| G Gly | 64 | 7.05 | 12.96 |
| H His | 4 | 1.06 | 0.81 |
| I Ile | 17 | 3.71 | 3.44 |
| K Lys | 20 | 4.95 | 4.05 |
| L Leu | 42 | 9.18 | 8.50 |
| M Met | 8 | 2.03 | 1.62 |
| N Asn | 32 | 7.05 | 6.48 |
| P Pro | 40 | 7.50 | 8.10 |
| Q Gln | 21 | 5.20 | 4.25 |
| R Arg | 19 | 5.73 | 3.85 |
| S Ser | 30 | 5.04 | 6.07 |
| T Thr | 26 | 5.08 | 5.26 |
| V Val | 25 | 4.78 | 5.06 |
| W Trp | 14 | 5.03 | 2.83 |
| Y Tyr | 7 | 2.21 | 1.42 |
| B Asx | 0 | 0.00 | 0.00 |
| Z Glx | 0 | 0.00 | 0.00 |
| X Xxx | 0 | 0.00 | 0.00 |
| . Ter | 1 | 0.00 | 0.20 |

The properties of the CSV-S fusion protein of SEQ ID NO: 20 are provided in the Tables below:

Nishikawa & Ooi 1987

| Analysis | Whole Protein |
| --- | --- |
| Molecular Weight | 51762.69 m.w. |
| Length | 494 |
| 1 microgram = | 19.319 pMoles |
| Molar Extinction coefficient | 90780 ± 5% |
| 1 A(280) = | 0.57 mg/ml |
| Isoelectric Point | 7.33 |
| Charge at pH 7 | 1.05 |

Whole Protein Composition Analysis

| Amino Acid(s) | Number count | % by weight | % by frequency |
| --- | --- | --- | --- |
| Charged (RKHYCDE) | 106 | 26.37 | 21.46 |
| Acidic (DE) | 38 | 8.83 | 7.69 |
| Basic (KR) | 39 | 10.69 | 7.89 |
| Polar (NCQSTY) | 134 | 28.17 | 27.13 |
| Hydrophobic (AILFWV) | 168 | 34.89 | 34.01 |
| A Ala | 52 | 7.14 | 10.53 |
| C Cys | 18 | 3.59 | 3.64 |
| D Asp | 24 | 5.34 | 4.86 |
| E Glu | 14 | 3.49 | 2.83 |
| F Phe | 17 | 4.83 | 3.44 |
| G Gly | 64 | 7.05 | 12.96 |
| H His | 4 | 1.06 | 0.81 |
| I Ile | 17 | 3.72 | 3.44 |
| K Lys | 20 | 4.95 | 4.05 |
| L Leu | 42 | 9.18 | 8.50 |
| M Met | 7 | 1.77 | 1.42 |
| N Asn | 32 | 7.05 | 6.48 |
| P Pro | 40 | 7.50 | 8.10 |
| Q Gln | 21 | 5.20 | 4.25 |
| R Arg | 19 | 5.73 | 3.85 |
| S Ser | 30 | 5.05 | 6.07 |
| T Thr | 26 | 5.08 | 5.26 |
| V Val | 26 | 4.98 | 5.26 |
| W Trp | 14 | 5.04 | 2.83 |
| Y Tyr | 7 | 2.21 | 1.42 |
| B Asx | 0 | 0.00 | 0.00 |
| Z Glx | 0 | 0.00 | 0.00 |
| X Xxx | 0 | 0.00 | 0.00 |
| . Ter | 1 | 0.00 | 0.20 |

The hybrid fusion protein CSV-S may, for example be prepared employing the plasmid pGF1-S2 (see FIG. 4 and the examples for further details), which when the appropriate sequence corresponding to CSV is inserted at the SmaI cloning site processes the insertion to proved the fusion protein CSV-S.

The nucleotide sequence for the hybrid fusion protein of SEQ ID NO: 17 is given in SEQ ID NO:16. The CSV portion of this sequence was codon optimized to optimize expression in yeast.

Alternatively the hybrid fusion protein CSV-S may, for example be prepared as described in Example 2.

An alternative nucleotide sequence for the hybrid fusion protein of the invention is given in SEQ ID NO: 19 and the amino acid sequence for the same is given in SEQ ID NO: 20.

The present invention also provides nucleotide sequences, for example DNA, encoding the proteins of the present invention.

The nucleotide sequences encoding the proteins of the present invention are, in one embodiment flanked by transcriptional control elements, preferably derived from yeast genes and incorporated into an expression vector.

An expression cassette for hybrid proteins of the invention may, for example, be constructed comprising the following features:

A promoter sequence, derived from, for example, the *S. cerevisiae* TDH3 gene.

A sequence encoding for the appropriate CSV-S hybrid fusion protein.

A transcription termination sequence contained within the sequence, derived from, for example, the *S. cerevisiae* ARG3 gene.

An example of a specific promoter is the promoter from the *S. cerevisiae* TDH3 gene Musti et al.

The invention also extends to vectors employed in the preparation of the hybrid fusion protein.

A suitable plasmid can then be employed to introduce the sequence encoding for the hybrid fusion protein into a suitable host for synthesis. An example of a suitable plasmid is pRIT15546 a 2 micron-based vector for carrying the CSV-S expression cassette, see plasmid map of same in FIG. 3.

Alternatively plasmids are known to person skilled in the art and/or described in the examples.

The plasmid will generally contain an in-built marker to assist selection, for example a gene encoding for antibiotic resistance or LEU and/or HIS auxotrophy.

In one aspect the plasmid is episomal ie the gene for the protein is not integrated into the DNA of the host.

The invention also relates to a host cell transformed with a vector according to the invention. Host cells can be prokaryotic or eukaryotic but preferably, are yeast, for example *Saccharomyces* (for example *Saccharomyces cerevisiae* such as DC5 in ATCC data base (accession number 20820), under the name RIT DC5 cir(o)). Depositor: Smith Kline-RIT) and non-*Saccharomyces* yeasts. These include *Schizosaccharomyces* (eg *Schizosaccharomyces pombe*) *Kluyveromyces* (eg *Kluyveromyces lactis*), *Pichia* (eg *Pichia pastoris*), *Hansenula* (eg *Hansenula polymorpha*), *Yarrowia* (eg *Yarrowia lipolytica*) and *Schwanniomyces* (eg *Schwanniomyces occidentalis*).

In one aspect the invention relates to a recombinant yeast strain Y1834 (and use thereof), which expresses a CSV-S hybrid fusion protein and/or immunogenic particles thereof, see Examples for preparation of the same.

In one aspect the invention relates to a recombinant yeast strain Y1835 (and use thereof), which expresses a CSV-S hybrid fusion protein and/or immunogenic particles thereof, see Examples for preparation of the same.

In an alternative aspect the invention relates to a recombinant yeast strain Y1840 (and use thereof), which expresses a CSV-S hybrid fusion protein and/or immunogenic particles thereof.

More specifically the invention relates to said yeast (or another yeast) comprising a nucleotide sequence encoding for the fusion protein of the invention, use of the yeasts for the preparation of said fusion protein, and processes involving the preparation of said fusion protein.

The nucleotide sequence (or a portion thereof, such as the portion encoding the hybrid protein but optionally not the portion encoding protein S) may be codon-optimized for expression in the relevant host such as yeast.

Codon-optimized in this context is intended to mean that the codons are modified to render them appropriate for expression in the relevant host. This may or may not be the most optimal codon selection, for example a sub-optimal optimized version may be selected if the expression of the same is greater than that of an optimal version.

In yeast cells once expressed, the hybrid fusion protein (comprising S antigen), is able to spontaneously assemble into a lipoprotein structure/particle composed of numerous monomers of said proteins.

These particles may also be referred to as Virus Like Particles (VLP). The particles may also be described as multimeric lipoprotein particles.

These particles can be prepared in a number of ways, for example by fusing each the *Plasmodium* derived antigens to another fusion partner, (for example the antigens of Hepatitis B virus or a viral structural protein) and expressing the same in a suitable host such as yeast or bacteria.

When the chosen recipient yeast strain also carries in its genome one or more integrated copies of a hepatitis B S expression cassette, the resulting strain synthesizes hybrid protein as a fusion proteins, and also non-fused S antigen. These may spontaneously be assembled into lipoprotein particles comprising monomers of the hybrid fusion protein and monomers of the S antigen.

Whilst not wishing to be bound by theory, the particles, for example when expressed in Y1834, are thought to consist essentially of units/monomers of the hybrid fusion protein, although it may be that the particle composition varies according the specific yeast employed.

Thus in some cases the lipoprotein particles may also contain the monomers of the unfused S antigen, for example as in the particles which are the result of preparation in the yeast Y1835.

Thus in one aspect the invention provides an immunogenic particle comprising hybrid fusion proteins of the invention.

Thus in one aspect the particle is a 'so-called' simple particle in that it consists essentially of units of the hybrid fusion protein. In an alternative aspect of the invention the immunogenic lipoprotein particle comprises one or more hybrid fusion proteins and one or more unfused protein S units, in a so-called double or mixed particle.

FIGS. 1 and 7 are electron micrographs of a lipoprotein particle according to this aspect of the invention, albeit prepared in different yeast.

The particles shown in the micrograph were purified by classical techniques using a cesium chloride and sucrose gradient, in particular using successive cesium chloride and sucrose gradients, more specifically: 1 sucrose gradient followed by 3 successive CsCl gradients.

The invention includes of methods of purifying said particles, for example employing a cesium chloride and sucrose gradient.

Additionally, it is hypothesized that, the surfactants used to liberate the protein from the cells may also assist in the stabilization of the lipoprotein particles. In a further aspect the lipoprotein particle comprises a surfactant. The surfactant may, for example be selected from TWEEN™ (such as TWEEN™ 20), BRIJ™, polyethylene glycol. The particle may, for example, comprise 1% or less, such as 0.5% or 0.1% by weight of surfactant.

It is hypothesized that the lipoprotein particles of the invention may contribute to further stimulating the immune response to the hybrid fusion protein in vivo.

The present invention also relates to vaccines comprising an immunoprotective amount of a protein or particle according to the invention in admixture with a suitable diluent or carrier.

The invention also extends to a composition comprising a hybrid/fusion protein or particle according to the invention and a viral vector comprising a malaria antigen, particularly a malaria antigen common with said particle, and optionally an adjuvant.

In the context of this specification, excipient refers to a component in a pharmaceutical formulation with no therapeutic effect in its own right. A diluent or carrier falls within the definition of an excipient.

In aspect the composition of the invention comprises a hybrid fusion protein and/or particle as described herein and an adjuvant.

In one embodiment the viral vector construct is as described in WO 2004/055187.

In one embodiment the said fusion proteins are in admixture and thus available as a single formulation. In an alternative embodiment the fusion proteins are prepared as separate formulations and are administered separately to the patient.

In a further aspect the invention relation to a combined treatment for *P. falciparum* and *P. vivax*, comprising:
an immunogenic fusion protein comprising an antigen derived from a CS protein of *P. vivax*, and an immunogenic fusion protein comprising an antigen derived from CS protein of *P. falciparum*.

In this aspect of the invention, antigen derived from the CS protein of *P. vivax* component of the fusion may be a naturally occurring (native) CS protein such as type I and or type II or a fragment thereof. Alternatively the antigen may be hybrid (chimeric) protein, as described above, such as the protein identified in SEQ ID NO: 13 and/or 15.

A fusion protein antigen component derived from *P. falciparum* may be prepared according to WO 93/10152 for example as RTS, S (wherein "S" represents an unfused monomer) or as RTS, both of which are suitable for use in this aspect of the invention.

In one embodiment the antigen derived from of *P. falciparum* comprises at least 4 repeat units of the central repeat region. More specifically this antigen comprises a sequence which contains at least 160 amino acids which is substantially homologous to the C-terminal portion of the CS protein. The CS protein may be devoid of the last 12 to 14 amino-acids from the C terminal.

More specifically the relevant fusion protein which comprises a portion of the CS protein of *P. falciparum* may substantial correspond to amino acids 207-395 of *P. falciparum* 7G8 fused in frame via a linear linker to the N-terminal of the S antigen. The linker may comprise a portion of preS2 from the S antigen.

More specifically the fusion protein derived from *P. falciparium* employed is that encoded for by the nucleotide sequence for the RTS expression cassette as provide in SEQ ID NO: 18.

Suitable S antigens, may comprise a preS2. An example of a suitable serotype is adw (Nature 280:815-819, 1979).

In one aspect the hybrid fusion proteins of the invention comprise a portion derived from a mutant S protein, for example as described in published US application No. 2006/194196 (also published as WO 2004/113369). This document describes a mutant labeled HDB05. In particular it describes comparisons of the mutant and the wild type protein in FIGS. 1 and 6 and genes for the mutant in FIGS. 4 and 5. Sequences 12 to 22 therein describe particular polypeptides of the mutant S protein. Each of the above is incorporated herein by reference.

The invention also relates to use of said combination for treatment, more particularly use as a vaccine for the prevention of malaria and method of treating a patient susceptible to *plasmodium* infection comprising administering an effective amount of each of the components either simultaneously or sequentially, thereby to treat or prevent Malaria.

In a further aspect the invention provides a combination for treatment comprising: an immunogenic hybrid antigen comprising a. at least one repeat unit derived from the central repeat section of a type I circumsporozoite protein of *P. vivax*,
b. at least one repeat unit derived from the central repeating section of a type II circumsporozoite protein of *P. vivax*, and an immunogenic fusion protein comprising an antigen derived from the CS protein of *P. falciparum*.

For example, wherein said hybrid antigen and said fusion protein are administered concomitantly for example they may be in admixture for administration simultaneously or alternatively may be formulated for administration sequentially.

In a further aspect there is provided a combination for treatment comprising: an immunogenic hybrid antigen comprising a. at least one repeat unit derived from the central repeat section of a type I circumsporozoite protein of *P. vivax*,
b. at least one repeat unit derived from the central repeating section of a type II circumsporozoite protein of *P. vivax*, and a viral vector encoding for a malaria antigen, such as said hybrid antigen.

For example, wherein said hybrid antigen and said viral vector are administered concomitantly, for example they may be admixed for administration simultaneously or alternatively may be formulated for administration sequentially.

As used herein the term "concomitantly" means wherein said combination of components are administered within a period of no more than 12 hours eg within a period of no more than 1 hour, typically on one occasion e.g. in the course of the same visit to the health professional, for example where they are administered sequentially or simultaneously.

The invention also includes a vaccine composition comprising said elements of each of these embodiments.

The invention also includes a vaccine kit comprising said elements for treating malaria.

The invention also extends to prime boost regimes comprising said elements, for example priming with antigen and/or particles from *P. falciparium* and boosting with antigen and/or particles from *P. vivax* and vice versa.

The prime boost regime may, for example comprise components derived solely or only from *P. vivax*.

In another embodiment the priming may be effected with plasmid/naked DNA and boosting is with antigen according to the invention and or vice versa.

Alternatively, priming may be effected with an appropriate viral vector and boosting with antigen according to the invention or vice versa.

General prime boost regimes are described below.

For example:

priming may be with an antigen (such as an adjuvanted antigen) comprising at least one type I repeat unit from the CS protein of *P. vivax* and at least one type II repeat unit from the CS protein of *P. vivax* and boosting may be with a viral vector encoding the same/corresponding antigen, priming may be with an antigen (such as an adjuvanted antigen) comprising at least one repeat unit or epitope from *P. vivax* and at least one repeat unit or epitope from the CS protein of *P. falciparum* and boosting may be with a viral protein encoding the same/corresponding antigen, priming may be with a viral vector encoding an antigen comprising at least one type I repeat unit from the CS protein of *P. vivax* and at least one type II repeat unit from the CS protein of *P. vivax* or comprising at least one repeat unit or epitope from *P. vivax* and at least one repeat unit or epitope from the CS protein of *P. falciparum* and boosting with the same/corresponding adjuvanted antigen in the form of a protein and/or immunogenic particle.

Antigen in these contexts includes hybrid fusion protein and/or immunogenic particles of the invention. In these prime boost regimes antigen will usually be adjuvanted.

In this/these aspect(s) of the invention the preferences described above for the hybrid protein derived from *P. vivax* also apply. Thus in one aspect the hybrid protein has the sequence in SEQ ID NO: 13.

RTS,S and antigen (in the form of an immunogenic particle) from *P. falciparum* can be prepared as described in WO 93/10152.

In one aspect the invention provides a replication deficient viral vector encoding a hybrid protein (or alternatively a hybrid fusion protein) according the invention. Suitable viral vectors may be derived from adeno viral vectors, adeno-associated viral vectors (AAVs), measles, lentiviruses, alphaviruses, baclovirusess, herpes simplex virus, and poxviruses such as cowpox, fowlpox, pigeonpox, canarypox, suipox and sheeppox/goatpox. Methodology for preparing adeno viral vectors encoding a malaria antigen is, for example, described in WO 2004/055187.

The protein encoded by the vector may, for example, be modified to prevent glycosylation of the protein during expression, for example certain serines may be replaced by alanine residues to reduce glycosylation.

Adenovirus

Adenoviral vectors of the present invention comprise one or more heterologous polynucleotides (DNA) which encode one or more immunogenic polypeptides.

Adenoviral vectors of use in the present invention may be derived from a range of mammalian hosts.

Adenoviruses (herein referred to as "Ad" or "Adv") have a characteristic morphology with an icosahedral capsid consisting of three major proteins, hexon (II), penton base (III) and a knobbed fibre (IV), along with a number of other minor proteins, VI, VIII, IX, IIIa and IVa2 (Russell W. C. 2000, Gen Viriol, 81:2573-2604). The virus genome is a linear, double-stranded DNA with a terminal protein attached covalently to the 5' termini, which have inverted terminal repeats (ITRs). The virus DNA is intimately associated with the highly basic protein VII and a small peptide termed mu. Another protein, V, is packaged with this DNA-protein complex and provides a structural link to the capsid via protein VI. The virus also contains a virus-encoded protease, which is necessary for processing of some of the structural proteins to produce mature infectious virus.

Over 100 distinct serotypes of adenovirus have been isolated which infect various mammalian species, 51 of which are of human origin. Thus one or more of the adenoviral vectors may be derived from a human adenovirus. Examples of such human-derived adenoviruses are Ad1, Ad2, Ad4, Ad5, Ad6, Ad11, Ad 24, Ad34, Ad35, Ad50/51 particularly Ad5, Ad11 and Ad35. The human serotypes have been categorised into six subgenera (A-F) based on a number of biological, chemical, immunological and structural criteria.

Although Ad5-based vectors have been used extensively in a number of gene therapy trials, there may be limitations on the use of Ad5 and other group C adenoviral vectors due to preexisting immunity in the general population due to natural infection. Ad5 and other group C members tend to be among the most seroprevalent serotypes. Immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

One such area of alternative serotypes are those derived from non human primates, especially chimpanzee adenoviruses. See U.S. Pat. No. 6,083,716 which describes the genome of two chimpanzee adenoviruses.

It has been shown that chimpanzee ("Pan" or "C") adenoviral vectors induce strong immune responses to transgene products as efficiently as human adenoviral vectors (Fitzgerald et al. J. Immunol. 170:1416).

Non human primate adenoviruses can be isolated from the mesenteric lymph nodes of chimpanzees. Chimpanzee adenoviruses are sufficiently similar to human adenovirus subtype C to allow replication of E1 deleted virus in HEK 293 cells. Yet chimpanzee adenoviruses are phylogenetically distinct from the more common human serotypes (Ad2 and Ad5). Pan 6 is less closely related to and is serologically distinct from Pans 5, 7 and 9.

Thus one or more of the adenoviral vectors may be derived from a non-human primate adenovirus eg a chimpanzee adenovirus such as one selected from serotypes Pan5, Pan6, Pan7 and Pan9.

Adenoviral vectors may also be derived from more than one adenovirus serotype, and each serotype may be from the same or different source. For example they may be derived from more than one human serotype and/or more than one non-human primate serotype. Methods for constructing chimeric adenoviral vectors are disclosed in WO2005/001103.

There are certain size restrictions associated with inserting heterologous DNA into adenoviruses. Human adenoviruses have the ability to package up to 105% of the wild type genome length (Bett et al 1993, J Virol 67 (10), 5911-21). The lower packaging limit for human adenoviruses has been shown to be 75% of the wild type genome length (Parks et al 1995, J Virol 71(4), 3293-8).

One example of adenoviruses useful in the present invention are adenoviruses which are distinct from prevalent naturally occurring serotypes in the human population such as Ad2 and Ad5. This avoids the induction of potent immune responses against the vector which limits the efficacy of subsequent administrations of the same serotype by blocking vector uptake through neutralizing antibody and influencing toxicity.

Thus, the adenovirus may be an adenovirus which is not a prevalent naturally occurring human virus serotype. Adenoviruses isolated from animals have immunologically distinct capsid, hexon, penton and fibre components but are phylogenetically closely related. Specifically, the virus may be a non-human adenovirus, such as a simian adenovirus and in particular a chimpanzee adenovirus such as Pan 5, 6, 7 or 9. Examples of such strains are described in WO 03/000283 and are available from the American Type Culture Collection, 10801 University Boulevard, Manassas, Va. 20110-2209, and other sources. Desirable chimpanzee adenovirus strains are Pan 5 [ATCC VR-591], Pan 6 [ATCC VR-592], and Pan 7 [ATCC VR-593].

Use of chimpanzee adenoviruses is thought to be advantageous over use of human adenovirus serotypes because of the lack of pre-existing immunity, in particular the lack of cross-neutralising antibodies, to adenoviruses in the target population. Cross-reaction of the chimpanzee adenoviruses with pre-existing neutralizing antibody responses is only present in 2% of the target population compared with 35% in the case of certain candidate human adenovirus vectors. The chimpanzee adenoviruses are distinct from the more common human subtypes Ad2 and Ad5, but are more closely related to human Ad4 of subgroup E, which is not a prevalent subtype. Pan 6 is less closely related to Pan 5, 7 and 9.

The adenovirus of the invention may be replication defective. This means that it has a reduced ability to replicate in non-complementing cells, compared to the wild type virus. This may be brought about by mutating the virus e.g. by deleting a gene involved in replication, for example deletion of the E1a, E1b, E3 or E4 gene.

The adenoviral vectors in accordance with the present invention may be derived from replication defective adenovirus comprising a functional E1 deletion. Thus the adenoviral vectors according to the invention may be replication defective due to the absence of the ability to express adenoviral E1a and E1b, i.e., are functionally deleted in E1a and E1b. The recombinant adenoviruses may also bear functional deletions in other genes [see WO 03/000283] for example, deletions in E3 or E4 genes. The adenovirus delayed early gene E3 may be eliminated from the adenovirus sequence which forms part of the recombinant virus. The function of E3 is not necessary to the production of the recombinant adenovirus particle. Thus, it is unnecessary to replace the function of this gene product in order to package a recombinant adenovirus useful in the invention. In one particular embodiment the recombinant adenoviruses have functionally deleted E1 and E3 genes. The construction of such vectors is described in Roy et al., Human Gene Therapy 15:519-530, 2004.

Recombinant adenoviruses may also be constructed having a functional deletion of the E4 gene, although it may be desirable to retain the E4 ORF6 function. Adenovirus vectors according to the invention may also contain a deletion in the delayed early gene E2a. Deletions may also be made in any of the late genes L1 through to L5 of the adenovirus genome. Similarly deletions in the intermediate genes IX and IVa may be useful.

Other deletions may be made in the other structural or non-structural adenovirus genes.

The above deletions may be used individually, i.e. an adenovirus sequence for use in the present invention may contain deletions of E1 only. Alternatively, deletions of entire genes or portions thereof effective to destroy their biological activity may be used in any combination. For example in one exemplary vector, the adenovirus sequences may have deletions of the E1 genes and the E4 gene, or of the E1, E2a and E3 genes, or of the E1 and E3 genes (such as functional deletions in E1a and E1b, and a deletion of at least part of E3), or of the E1, E2a and E4 genes, with or without deletion of E3 and so on. Such deletions may be partial or full deletions of these genes and may be used in combination with other mutations, such as temperature sensitive mutations to achieve a desired result.

The adenoviral vectors can be produced on any suitable cell line in which the virus is capable of replication. In particular, complementing cell lines which provide the factors missing from the viral vector that result in its impaired replication characteristics (such as E1 and/or E4) can be used. Without limitation, such a cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources, such as PER.C6© cells, as represented by the cells deposited under ECACC no. 96022940 at the European Collection of Animal Cell Cultures (ECACC) at the Centre for Applied Microbiology and Research (CAMR, UK) or Her 96 cells (Crucell).

The invention extends to use of known cell lines for the preparation of a viral vector encoding a protein of the present invention.

The polynucleotide sequences which encode immunogenic polypeptides may be codon optimised for mammalian cells. Such codon-optimisation is described in detail in WO 05/025614 for example, starting at page 37.

In one embodiment of the present invention wherein the viral vector comprising the polynucleotide constructs wherein said constructs comprise an N-terminal leader sequence. The signal sequence, transmembrane domain and cytoplasmic domain are individually all optionally present or deleted. In one embodiment of the present invention all these regions are present but modified.

A promoter for use in the adenoviral vector according to the invention may be the promoter from HCMV IE gene, for example wherein the 5' untranslated region of the HCMV IE gene comprising exon 1 is included and intron A is completely or partially excluded as described in WO 02/36792.

When several antigens are fused into a fusion protein, such protein would be encoded by a polynucleotide under the control of a single promoter.

In an alternative embodiment of the invention, several antigens may be expressed separately through individual promoters, each of said promoters may be the same or different. In yet another embodiment of the invention some of the antigens may form a fusion, linked to a first promoter and other antigen(s) may be linked to a second promoter, which may be the same or different from the first promoter.

Thus, the adenoviral vector may comprise one or more expression cassettes each of which encode one antigen under the control of one promoter. Alternatively or additionally it may comprise one or more expression cassettes each of which encode more than one antigen under the control of one promoter, which antigens are thereby expressed as a fusion. Each expression cassette may be present in more than one locus in the adenoviral vector.

The polynucleotide or polynucleotides encoding immunogenic polypeptides to be expressed may be inserted into any of the adenovirus deleted regions, for example into the E1 deleted region.

Although two or more polynucleotides encoding immunogenic polypeptides may be linked as a fusion, the resulting protein may be expressed as a fusion protein, or it may be expressed as separate protein products, or it may be expressed as a fusion protein and then subsequently broken down into smaller subunits.

Immunogenic in the context of this specification is intended to refer to the ability to illicit an immune response. This response may be when the protein in administered in an appropriate formulation, which may include/require a suitable adjuvant. A booster comprising a dose similar or less than the original dose may be required to obtain the required immunogenic response (including boosting with a different entity ie heterologous boosting).

The composition/pharmaceutical formulations according to the invention may also include in admixture one or more further antigens, such as those derived from *P. falciparium* and/or *P. vivax*, for example wherein the antigen is selected from DBP, PvTRAP, PvMSP2, PvMSP4, PvMSP5, PvMSP6, PvMSP7, PvMSP8, PvMSP9, PvAMA1 and RBP or fragment thereof.

Other example, antigens derived from *P falciparum* include, PfEMP-1, Pfs 16 antigen, MSP-1, MSP-3, LSA-1, LSA-3, AMA-1 and TRAP. Other *Plasmodium* antigens include *P. falciparum* EBA, GLURP, RAP1, RAP2, Sequestrin, Pf332, STARP, SALSA, PfEXP1, Pfs25, Pfs28, PFS27/25, Pfs48/45, Pfs230 and their analogues in other *Plasmodium* spp.

In the vaccine of the invention, an aqueous solution of the hybrid antigen may be used directly. Alternatively, the protein with or without prior lyophilisation can be mixed or absorbed with adjuvants, which include but are not limited to alum, muramyl dipeptide, saponins such as Quil A.

Particular adjuvants are those selected from the group of metal salts, oil in water emulsions, Toll like receptors agonist, (in particular Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof with the proviso that metal salts are only used in combination with another adjuvant and not alone unless they are formulated in such a way that not more than about 60% of the antigen is adsorbed onto the metal salt. More specifically, not more than about 50%, for example 40% of the antigen is adsorbed onto the metal salt, and in one embodiment not more than about 30% of the antigen is adsorbed onto the metal salt. The level of antibody adsorbed onto the metal salt may be determined by techniques well known in the art. The level of free antigen may be increased by, for example, formulating the composition in the presence of phosphate ions, such as phosphate buffered saline, or by increasing the ratio of antigen to metal salt. In one embodiment the adjuvant does not include a metal salt as sole adjuvant. In one embodiment the adjuvant does not include a metal salt.

In an embodiment the adjuvant is a Toll like receptor (TLR) 4 ligand, for example an agonist such as a lipid A derivative, in particular monophosphoryl lipid A or more specifically 3 Deacylated monophoshoryl lipid A (3D-MPL).

3 Deacylated monophosphoryl lipid A is known from U.S. Pat. No. 4,912,094 and UK patent application No. 2,220,211 (Ribi) and is available from Ribi Immunochem, Montana, USA. 3D-MPL is sold under the trademark MPL® by Corixa corporation and primarily promotes CD4+ T cell responses with an IFN-g (Th1) phenotype. It can be produced according to the methods disclosed in GB 2 220 211 A. Chemically it is a mixture of 3-deacylated monophosphoryl lipid A with 3, 4, 5 or 6 acylated chains. Generally in the compositions of the present invention small particle 3D-MPL is used. Small particle 3D-MPL has a particle size such that it may be sterile-filtered through a 0.22 µm filter. Such preparations are described in International Patent Application No. WO 94/21292.

Synthetic derivatives of lipid A are known and thought to be TLR 4 agonists including, but not limited to:

OM174 (2-deoxy-6-O-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026).

OM 294 DP (3S,9R)-3-[(R)-dodecanoyloxytetradecanoylamino]-4-oxo-5-aza-9(R)-[(R)-3-hydroxytetradecanoylamino]decan-1,10-diol, 1,10-bis(dihydrogenophosphate) (WO 99/64301 and WO 00/0462).

OM 197 MP-Ac DP (3S,9R)-3-[(R)-dodecanoyloxytetradecanoylamino]-4-oxo-5-aza-9-[(R)-3-hydroxytetradecanoylamino]decan-1,10-diol, 1-dihydrogenophosphate 10-(6-aminohexanoate) (WO 01/46127).

Typically when 3D-MPL is used the antigen and 3D-MPL are delivered with alum or presented in an oil in water emulsion or multiple oil in water emulsions. The incorporation of 3D-MPL is advantageous since it is a stimulator of effector T-cells responses. Alternatively the 3D-MPL may be formulated as liposomes.

Other TLR4 ligands which may be used are alkyl Glucosaminide phosphates (AGPs) such as those disclosed in WO 9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants.

Another immunostimulant for use in the present invention is Quil A and its derivatives. Quil A is a saponin preparation isolated from the South American tree *Quilaja Saponaria Molina* and was first described as having adjuvant activity by Dalsgaard et al. in 1974 ("Saponin adjuvants", Archiv. für die gesamte Virusforschung, Vol. 44, Springer Verlag, Berlin, p 243-254). Purified fragments of Quil A have been isolated by HPLC which retain adjuvant activity without the toxicity associated with Quil A (EP 0 362 278), for example QS7 and QS21 (also known as QA7 and QA21). QS21 is a natural saponin derived from the bark of *Quillaja saponaria Molina* which induces CD8+ cytotoxic T cells (CTLs), Th1 cells and a predominant IgG2a antibody response.

Particular formulations of QS21 have been described which further comprise a sterol (WO 96/33739). The ratio of QS21:sterol will typically be in the order of 1:100 to 1:1 weight to weight.

Generally an excess of sterol is present, the ratio of QS21:sterol being at least 1:2 w/w. Typically for human administration QS21 and sterol will be present in a vaccine in the range of about 1 µg to about 100 µg, such as about 10 µg to about 50 µg per dose.

The liposomes generally contain a neutral lipid, for example phosphatidylcholine, which is usually non-crystalline at room temperature, for example eggyolk phosphatidylcholine, dioleoyl phosphatidylcholine or dilauryl phosphatidylcholine. The liposomes may also contain a charged lipid which increases the stability of the lipsome-QS21 structure for liposomes composed of saturated lipids. In these cases the amount of charged lipid is often 1-20% w/w, such as 5-10%. The ratio of sterol to phospholipid is 1-50% (mol/mol), such as 20-25%.

These compositions may contain MPL (3-deacylated mono-phosphoryl lipid A, also known as 3D-MPL). 3D-MPL is known from GB 2 220 211 (Ribi) as a mixture of 3 types of de-O-acylated monophosphoryl lipid A with 4, 5 or 6 acylated chains and is manufactured by Ribi Immunochem, Montana.

Generally in compositions of the invention small particle 3D-MPL, which has a particle size such that it may be sterile-filtered through a 0.22 µm filter, is employed. Such preparations are described in WO 94/21292.

The saponins may be separate in the form of micelles, mixed micelles (generally, but not exclusively with bile salts) or may be in the form of ISCOM matrices (EP 0 109 942 B1), liposomes or related colloidal structures such as worm-like or ring-like multimeric complexes or lipidic/layered structures and lamellae when formulated with cholesterol and lipid, or in the form of an oil in water emulsion (for example as in WO 95/17210). The saponins may often be associated with a metallic salt, such as aluminium hydroxide or aluminium phosphate (WO 98/15287).

Usually, the saponin is presented in the form of a liposome, ISCOM or an oil in water emulsion.

Immunostimulatory oligonucleotides may also be used. Examples oligonucleotides for use in adjuvants or vaccines of the present invention include CpG containing oligonucleotides, generally containing two or more dinucleotide CpG motifs separated by at least three, more often at least six or more nucleotides. A CpG motif is a cytosine nucleotide followed by a guanine nucleotide. The CpG oligonucleotides are typically deoxynucleotides. In one embodiment the internucleotide in the oligonucleotide is phosphorodithioate, or more preferably a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. No. 5,666,153, U.S. Pat. No. 5,278,302 and WO 95/26204.

Examples of oligonucleotides are as follows:

```
                                           [SEQ ID NO: 24]
TCC ATG ACG TTC CTG ACG TT (CpG 1826)

[SEQ ID NO: 25]
TCT CCC AGC GTG CGC CAT (CpG 1758)

[SEQ ID NO: 26]
ACC GAT GAC GTC GCC GGT GAC GGC ACC ACG

[SEQ ID NO: 27]
TCG TCG TTT TGT CGT TTT GTC GTT (CpG 2006)

[SEQ ID NO: 28]
TCC ATG ACG TTC CTG ATG CT (CpG 1668)

[SEQ ID NO: 29]
TCG ACG TTT TCG GCG CGC GCC G (CpG 5456),
``` the sequences may contain phosphorothioate modified internucleotide linkages.

Alternative CpG oligonucleotides may comprise one or more sequences above in that they have inconsequential deletions or additions thereto.

The CpG oligonucleotides may be synthesized by any method known in the art (for example see EP 468520). Conveniently, such oligonucleotides may be synthesized utilising an automated synthesizer.

Examples of a TLR 2 agonist include peptidoglycan or lipoprotein. Imidazoquinolines, such as Imiquimod and Resiquimod are known TLR7 agonists. Single stranded RNA is also a known TLR agonist (TLR8 in humans and TLR7 in mice), whereas double stranded RNA and poly IC (polyinosinic-polycytidylic acid—a commercial synthetic mimetic of viral RNA) are exemplary of TLR 3 agonists. 3D-MPL is an example of a TLR4 agonist whilst CpG is an example of a TLR9 agonist.

An immunostimulant may alternatively or in addition be included. In a one embodiment this immunostimulant will be 3 deacylated monophosphoryl lipid A (3D-MPL).

Adjuvants combinations include 3D-MPL and QS21 (EP 0 671 948 B1), oil in water emulsions comprising 3D-MPL and QS21 (WO 95/17210, WO 98/56414), or 3D-MPL formulated with other carriers (EP 0 689 454 B1) including liposomes. Other preferred adjuvant systems comprise a combination of 3D-MPL, QS21 and a CpG oligonucleotide as described in U.S. Pat. No. 6,558,670 and U.S. Pat. No. 6,544,518.

In one aspect the adjuvant comprises 3D-MPL.
In one aspect the adjuvant comprises QS21.
In one aspect the adjuvant comprises CpG.
In one aspect the adjuvant comprises QS21 and 3D-MPL.
In one aspect the adjuvant comprises QS21, 3D-MPL and CpG In one aspect the adjuvant is formulated as an oil in water emulsion.

In one aspect the adjuvant is formulated as liposomes.

In one embodiment of the present invention provides a vaccine comprising a hybrid protein as herein described, such as CSV-S in combination with 3D-MPL and a carrier. Typically the carrier will be an oil in water emulsion or alum.

More specifically the hybrid protein is presented as a particle or mixed particle as herein described.

The protein of the present invention may also be encapsulated into microparticles such as liposomes.

Vaccine preparation is generally described in New Trends and Developments in Vaccines, edited by Voller et al., University Park Press, Baltimore, Md., U.S.A., 1978. Encapsulation within liposomes is described, for example, by Fullerton, U.S. Pat. No. 4,235,877.

The amount of the protein of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally, it is expected that each does will comprise 1-1000 µg of protein, for example 1-200 µg such as 10-100 µg more particularly 10-40 µg. An optimal amount for a particular vaccine can be ascertained by standard studies involving observation of antibody titres and other responses in subjects. Following an initial vaccination, subjects will preferably receive a boost in about 4 weeks, followed by repeated boosts every six months for as long as a risk of infection exists. The immune response to the protein of this invention is enhanced by the use of adjuvant and or an immunostimulant.

The amount of 3D-MPL used is generally small, but depending on the vaccine formulation may be in the region of 1-1000 µg per dose, generally 1-500 µg per dose, and more such as between 1 to 100 µg per dose (10, 20, 30, 40, 50, 60, 70, 80 or 90 µg per dose).

The amount of CpG or immunostimulatory oligonucleotides in the adjuvants or vaccines of the present invention is generally small, but depending on the vaccine formulation may be in the region of 1-1000 µg per dose, generally 1-500 µg per dose, and more such as between 1 to 100 µg per dose (10, 20, 30, 40, 50, 60, 70, 80 or 90 µg per dose).

The amount of saponin for use in the adjuvants of the present invention may be in the region of 1-1000 µg per dose, generally 1-500 µg per dose, more such as 1-250 µg per dose, and more specifically between 1 to 100 µg per dose (10, 20, 30, 40, 50, 60, 70, 80 or 90 µg per dose).

In a further aspect the invention provides a vaccine combination providing immunoprotection against malaria caused by *P. falciparum* and/or *P. vivax* comprising a hybrid protein derived from CS protein of *P. vivax* such as described herein.

In one aspect there is provided a vaccine comprising immunogenic particles as described herein, and optionally further comprising immunogenic particles of TRS, S in admixture (as described in WO 93/10152) and an appropriate immunostimulatory adjuvant.

The formulations of the present invention may be used in treatment for both prophylactic and therapeutic purposes.

Accordingly the invention provides use of any aspect of the invention described herein for treatment, in particular a vaccine composition as described herein for use in medicine.

A further aspect of the present invention is to provide a process for the preparation of hybrid protein of the invention, which process comprises expressing a nucleotide sequence encoding the protein, in a suitable host, preferably a yeast, and recovering the product.

The invention also extends to methods of preparing pharmaceutical composition such as vaccines employing one or more aspects described herein.

A further aspect of the invention lies in a method of treating a patient susceptible to *plasmodium* infection by administering an effective amount of a vaccine as hereinbefore described.

Vaccine includes a parenteral vaccine.

Thus the invention extends to use of the antigens such as hybrid fusion proteins and/or lipoprotein particles of the invention and compositions comprising same for treatment and particular in use in the manufacture of a medicament for the treatment/prevention of malaria, such as malaria caused by P. vivax and/or P. falciparum.

Proteins and/or viral vectors encoding same may be administered in prime boost regimes, for example as specifically described in WO 2004/037189.

In the context of this specification "comprising" is to be interpreted as "including".

Aspects of the invention comprising certain elements are also intended to extend to said aspects "consisting" or "consisting essentially" of the relevant elements.

EXAMPLES

Example 1

Description of Strain Y1834

The yeast recombinant strain Y1834 expresses the CSV-S fusion protein. It consists of the *Saccharomyces cerevisiae* host strain DC5 transformed with the recombinant expression vector pRIT15546.

DC5 is a laboratory yeast strain (ATCC No: 20820) with the following genotype: leu2-3, leu2-112, his3, can1-11. The double leu-2 mutation permits selection for the uptake and maintenance of the pRIT15546 vector which carries a functional LEU-2 gene copy. Only those cells carrying a vector with a LEU-2 gene can grow when leucine is absent from the growth medium.

The vector pRIT15546 is a yeast episomal expression vector (2μ-based vector) carrying the CSV-S expression cassette. The recombinant expression is driven by a promoter derived from the yeast TDH3 gene (constitutive expression). The construction of pRIT15546 vector is detailed below.

Construction of pRIT15546 vector.
  A CSV synthetic gene, with an appropriate codon usage for yeast expression was constructed and sub-cloned into pUC57 vector (GenBank/EMBL accession number Y14837). The resulting plasmid pUC57/CSV and the yeast expression vector pGf1-S2 were both restricted with the appropriate enzyme. The vector pGf1-S2 was constructed (at GSK) by a multistep cloning procedure. This vector, which already carries an S expression cassette, allows the construction of fusion genes, as N-terminal in-frame fusion with the S gene of Hepatitis B virus. The final expression vector, after sequence verification, was named pRIT15546 (FIG. 3)
Transformation of strain DC5.
  The leu- and his-auxotrophic DC5 strain was transformed with the recombinant plasmid pRIT15546, by using yeast standard protocol. Transformed cells were plated on agar selective plates. One transformant was selected and received the official designation Y1834.
Expression of the Recombinant Protein:
  Y1834 is grown, at 30° C., in YNB (Yeast Nitrogen Base available from Kracker Scientific Inc) minimal medium supplemented to a final concentration 8 μg/ml histidine to an O.D (620 nm) of about 0.5 (here 0.770). Then cells are harvested and cellular extracts are prepared.

Extract Preparation:
  Cells are resuspended in Breaking Buffer and mechanically disrupted (glass beads). Extract is centrifuged for 5-10 minutes at 5000 rpm. Supernatant fraction is run on SDS-PAGE 4-20%.
Breaking Buffer: 50 mM phosphate Na buffer (PH:7.5)
  4 mM EDTA
  TWEEN™-20 0.5%
  +proteases inhibitor cocktail (Complete/ROCHE)
Cell concentration: 100 ml culture (OD: 0.5) in 5 ml breaking buffer=concentration of 10 OD unit/ml.
Crude extract clarification: extract centrifuged 5-10 minutes/ 5000 rpm
Detection of Recombinant Protein
  Clarified extracts are run on SDS-PAGE 4-20%, proteins transferred to nitrocellulose membrane and subjected to immunostaining See FIG. 2A-B.
Western blot analysis:
  Reagent=Mouse monoclonal antibody anti-S (prepared by GSK Biologicals)-(dilution: 1/500)
  Anti-S antibodies which are commercially available may be substituted for those employed in this method. Alternatively anti-CSV antibodies may be employed, for example those known as MR4 available from NIH.
CSV-S fusion protein:
  MW theoretical: 51794 Daltons
  MW apparent: 55 kDa Example 2

Description of Strain Y1840

The *Pichia pastoris* strain Y1840 expresses the CSV-S fusion protein. Strain Y1840 contains four copies of the CSV-S fusion gene, integrated in the genome. To obtain a strain expressing the CSV-S fusion protein, the *Pichia pastoris* strain GS115 was transformed with an integrative linear DNA fragment which carries the CSV-S cassette and the functional HIS4 gene.

GS115 is a laboratory yeast strain (ATCC No: 20864) with the following genotype: his4. The his4 mutation permits selection for the uptake of the pRIT15607-derived linear DNA fragment which carries the CSV-S cassette and the functional HIS4 gene.

The vector pRIT15607 is a *Pichia pastoris* integrative expression vector carrying the CSV-S expression cassette. The recombinant expression is driven by the strong, tightly regulated methanol inducible AOX1 promoter. The construction of pRIT15607 vector is detailed below.

Construction of pRIT15607 vector.
  The CSV-S fusion gene, present on pRIT15546, was amplified by PCR and cloned into the pGEM-T Easy intermediate vector (Promega, cat No: #A1360). After sequence verification the recombinant plasmid was digested with the appropriate restriction enzymes and cloned into the pHIL-D2 *Pichia pastoris* integrative vector. The final expression vector, after sequence verification, was named pRIT15607 (FIG. 5). The CSV-S fusion protein encoded by pRIT15607 plasmid is almost identical to the sequence detailed in SEQ ID NO: 17, except that methionine 2 is replaced by a valine (see SEQ ID NO: 19 and SEQ ID NO: 20). Digestion of pRIT15607 with NotI endonuclease liberates a 6816 by linear fragment which can be integrated into the yeast genome by homologous recombination at the resident AOX1 locus.

Transformation of strain GS115.

The GS115 host strain was transformed with the recombinant plasmid pRIT15607. Prior to transformation the integrative vector was restricted with NotI in order to release a linear DNA fragment carrying the expression cassette and the HIS4 selective marker. NotI restriction will favor integration at the AOX1 locus. Transformed cells were plated on agar selective plates. Multicopy integrant clones were selected by quantitative dot blot analysis. Among the clones selected has having a high copy number of integrated CSV-S expression cassettes, one of them showing the highest expression level for CSV-S recombinant protein was selected and given the official designation Y1840. This clone carries four copies of the CSV-S fusion gene.

Expression of the Recombinant Protein:

Y1840 is grown, at 30° C., in YNB (Yeast Nitrogen Base available from Kracker Scientific Inc) minimal medium supplemented with 1% glycerol as a carbon source to an O.D. (620 nm) of about 0.5 (0.709 in this case). Then cells are harvested and resuspended in the same volume of YNB medium supplemented with 1% methanol as a carbon source (as inducer) and incubated at 30° C. for about 16 hours.

Extract Preparation:

Methanol induced cells are centrifuged, cell pellets resuspended in Breaking Buffer and mechanically disrupted (glass beads or French press). Extract is centrifuged for 5-10 minutes at 5000 rpm. Supernatant fraction is run on SDS-PAGE 12.5%.

Breaking Buffer: 60 mM $Na_2HPO_4$
   40 mM $NaH_2PO_4$
   1 mM $MgSO_4$
   10 Mm KCl
   TWEEN™-20 0.5%
   2 Mm PMSF Cell concentration: 100 ml culture (OD:0.5) in 2.5 ml breaking buffer=concentration of 20 OD unit/ml.

Crude extract clarification: extract centrifuged 5-10 minutes/ 5000 rpm

Detection of Recombinant Protein

Clarified extracts are run on SDS-PAGE 12.5%, proteins transferred to nitrocellulose membrane and subjected to immunostaining See FIG. 6.

Western blot analysis:

Reagent=Mouse monoclonal antibody anti-S (prepared by GSK Biologicals)-(dilution: 1/250)

Anti-S antibodies which are commercially available may be substituted for those employed in this method. Alternatively anti-CSV antibodies may be employed, for example those known as MR4 available from NIH.

CSV-S fusion protein: MW theoretical: 51762 Daltons
   MW apparent: 55 kDa

Example 3

Description of Strain Y1835

The yeast recombinant strain Y1835 simultaneously expresses the CSV-S fusion protein and the S antigen. To obtain a strain co-expressing CSV-S and S proteins, the Saccharomyces cerevisiae strain Y1295, which already carries five integrated copies of S expression cassettes, was transformed with the recombinant integrative expression vector pRIT15582.

The strain Y1295 was constructed at GSK by a multistep transformation procedure. The construction of Y1295 strain is described in WO 93/10152. Strain Y1295 has the following genotype: leu2-3, leu2-112, gall. The leu-2 mutation permits selection for the uptake of pRIT15582-derived linear DNA fragment which carries the CSV-S cassette and the functional LEU2 gene.

The vector pRIT15582 is a yeast integrative expression vector (Ty-based vector) carrying the CSV-S expression cassette. The recombinant expression is driven by a promoter derived from the yeast TDH3 gene (constitutive expression). The construction of pRIT15582 vector is detailed below.

Construction of pRIT15582 integrative vector.

The starting material used to construct pRIT15582 vector was the expression plasmid pRIT15546 (FIG. 3). The construction of this plasmid is described in example 1. Digestion of pRIT 15546 with HindIII endonuclease liberates a 3706 by long DNA fragment corresponding to the complete CSV-S expression cassette (pTDH3+CSV-S+tARG3). This HindIII DNA fragment (after filling with T4 DNA polymerase) was inserted on the Ty-based integrative vector pRIT13144 at the unique SalI cloning site (SalI restricted/T4 treated). The resulting plasmid pRIT15582 contains, in addition to the expression cassette, the yeast LEU2 gene as selective marker (FIG. 8). Digestion of pRIT15582 with XhoI endonuclease liberates a 8500 by linear fragment shown in FIG. 4 which can be integrated into the yeast genome by homologous recombination of the free ends with resident Ty elements.

Transformation of strain Y1295.

To obtain a strain expressing both S and CSV-S proteins, strain Y1295 was transformed with the 8500 bp linear XhoI fragment (FIG. 9) with selection for Leu+ colonies. Several integrants containing sets of both expression cassettes present in the genome at various ratio were obtained. One transformant carrying four copies of CSV-S cassettes was selected and given the official designation Y1835.

Expression of the Recombinant Protein:

Y1835 is grown, at 30° C., in YNB (Yeast Nitrogen Base available from Kracker Scientific Inc) minimal medium to an O.D (620 nm) of about 0.5 (0.8). Then cells are harvested and cellular extracts are prepared.

Analysis of Expression Products by Immunoblotting:

Extract Preparation:

Cells are re-suspended in Breaking Buffer and mechanically disrupted (glass beads). Extract is centrifuged for 5-10 minutes at 5000 rpm. Supernatant fraction is run on SDS-PAGE 12.5%.

Breaking Buffer: 50 mM phosphate Na buffer (PH:7.5)
   4 mM EDTA
   TWEEN™-20 0.5%
   +proteases inhibitor cocktail (Complete/ROCHE)

Cell concentration: 100 ml culture (OD:0.5) in 2.5 ml breaking buffer=concentration of 20 OD unit/ml.

Crude extract clarification: extract centrifuged 5-10 minutes/ 5000 rpm

Detection of Recombinant Protein

Clarified extracts are run on SDS-PAGE 12.5%, proteins transferred to nitrocellulose membrane and subjected to immunostaining Western blot analysis (FIG. 10):

Reagents: 1/ Mouse monoclonal antibody anti-S (prepared by GSK Biologicals)-(dilution: 1/250)
   2/ Rabbit polyclonal antibody anti-CSV (kindly provided by WRAIR)-dilution 1/20,000.

Anti-S antibodies as well as anti-*P. vivax*/CSP antibodies which are commercially available may be substituted for those employed in this method.

REFERENCE (1) Harford N, Cabezon T, Colau B, et al., "Construction and Characterization of a *Saccharomyces Cerevisiae* Strain (RIT4376) Expressing Hepatitis B Surface Antigen", *Postgrad Med* J 63, Supp. 2: 65-70, 1987.
(2) Jacobs E, Rutgers T, Voet P, et al., "Simultaneous Synthesis and Assembly of Various Hepatitis B Surface Proteins in *Saccharomyces cerevisiae*", *Gene* 80: 279-291, 1989.
(3) Vieira J and Messing J, "The pUC plasmids, an M13mp7-Derived System for Insertion Mutagenesis and Sequencing with Synthetic Universal Primers", *Gene* 19: 259-268, 1982.
(4) Hinnen A, Hicks J B, and Fink G R, "Transformation of Yeast", *Proc Natl Acad Sci USA* 75: 1929-1933, 1980.
(5) Broach J R, Strathern J N, and Hicks J B, "Transformation in Yeast Development of a Hybrid Cloning Vector and Isolation of the CAN 1 Gene", *Gene* 8: 121-133, 1979.
(6) Zhang H, et al., "Double Stranded SDNA Sequencing as a Choice for DNA Sequencing", *Nucleic Acids Research* 16: 1220, 1988.
(7) Dame J B, Williams J L. Mc Cutchan T F, et al., "Structure of the Gene Encoding the Immunodominant Surface Antigen on the Sporozoites of the Human Malaria Parasite *Plasmodium falciparum*", *Science* 225: 593-599, 1984.
(8) Valenzuela P, Gray P, Quiroga M, et al., "Nucleotide Sequences of the Gene Coding for the Major Protein of Hepatitis B Virus Surface Antigen", *Nature* 280: 815-819, 1979.
(9) In S S, Kee-Hoyung L, Young R K, et al., "comparison of Immunological Responses to Various Types of Circumsporozoite Proteins of *Plasmodium vivax* in Malaria Patients of Korea", Microbiol. Immunol. 48(2): 119-123, 2004; Microbiol. Immunol. 2004; 48(2): 119-123.
(10) Rathore D, Sacci J B, de la Vega P, et al., <<Binding and Invasion of Liver Cells by *Plasmodium falciparum* Sporozoites", J. Biol. Chem. 277(9): 7092-7098, 2002. Rathore et al., 2002, J. Biol. Chem. 277, 7092-8

The invention claimed is:

1. An immunogenic hybrid fusion protein comprising:
   a. at least one repeat unit from the repeating region of a type I circumsporozoite (CS) protein of P. vivax, wherein the at least one type I repeat unit is selected from one or more monomer sequences as set forth in SEQ ID NOs: 3 and 5-9,
   b. at least one repeat unit from the repeating region of a type II circumsporozoite (CS) protein of P. vivax, wherein the at least one type II repeat unit is selected from one or more monomer sequences as set forth in SEQ ID NOs: 10 and 14, and
   c. surface antigen S from Hepatitis B virus.

2. The immunogenic hybrid fusion protein of claim 1, wherein the hybrid fusion protein further comprises an N-terminus fragment from CS protein of P. vivax comprising the fragment known as Region I as set forth in SEQ ID NO: 1.

3. The immunogenic hybrid fusion protein of claim 1, wherein the hybrid fusion protein further comprises a C-terminus fragment from CS protein of P. vivax comprising the section known as Region II as set forth in SEQ ID NO: 2.

4. The immunogenic hybrid fusion protein of claim 1, wherein the at least one type I repeat unit comprises at least 9 of the monomer sequences.

5. The immunogenic hybrid fusion protein of claim 1, wherein the at least one type II repeat unit comprises one of the monomer sequences.

6. The immunogenic hybrid fusion protein of claim 1, which further comprises the 12 amino acid insertion located at the end of the repeat region found in Asian strains of P. vivax.

7. The immunogenic hybrid fusion protein of claim 6, wherein the 12 amino acid insertion has the sequence as set forth in SEQ ID NO: 11.

8. The immunogenic hybrid fusion protein of claim 1, wherein the Hepatitis B S antigen is from an adw serotype.

9. The immunogenic hybrid fusion protein of claim 1, which further comprises one or more further antigens from P. falciparium and/or P. vivax.

10. The immunogenic hybrid fusion protein of claim 1, which comprises the hybrid circumsporozoite protein sequence as set forth in SEQ ID NO: 13.

11. A composition comprising the hybrid fusion protein according to claim 1 and an adjuvant.

12. The composition of claim 11, wherein the adjuvant is selected from the group of:
   metal salts,
   oil in water emulsions,
   toll like receptors agonist,
   saponins,
   CpG containing oligonucleotides,
   3D-MPL,
   (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate),
   DP (3S,9R)-3-[(R)-dodecanoyloxytetradecanoylamino]-4-oxo-5-aza-9(R)-[(R)-3-hydroxytetradecanoylamino] decan-1,10-diol, 1,10-bis(dihydrogenophosphate),
   MP-Ac DP (3S,9R)-3-[(R)-dodecanoyloxytetradecanoylamino]-4-oxo-5-aza-9-[(R)-3-hydroxytetradecanoylamino]decan-1,10-diol, 1-dihydrogenophosphate 10-(6-aminohexanoate), and
   combinations thereof.

13. The composition of claim 11, wherein the adjuvant is selected from the group of:
   a saponin associated with a metallic salt,
   3D-MPL, QS21 and a CpG oligonucleotide,
   saponin in the form of a liposome, and
   an ISCOM.

14. The composition of claim 11, which further comprises one or more further antigens from P. falciparium and/or P. vivax in admixture.

15. The composition of claim 11, which further comprises a surfactant.

16. A multimeric lipoprotein particle comprising the hybrid fusion protein of claim 1.

17. A composition comprising the particle of claim 16, and at least one excipient/carrier.

18. The composition of claim 17, which further comprises an adjuvant.

19. The composition of claim 18, wherein the adjuvant is selected from the group of:
   metal salts,
   oil in water emulsions,
   toll like receptors agonist,
   saponins,
   CpG containing oligonucleotides,
   3D-MPL,
   (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate),
   DP (3S,9R)-3-[(R)-dodecanoyloxytetradecanoylamino]-4-oxo-5-aza-9(R)-[(R)-3-hydroxytetradecanoylamino] decan-1,10-diol, 1,10-bis(dihydrogenophosphate), MP-Ac DP (3S,9R)-3-[(R)-dodecanoyloxytetradecanoylamino]-4-oxo-5-aza-9-[(R)-3-hydroxytetradecanoylamino]decan-1,10-diol, 1-dihydrogenophosphate 10-(6-aminohexanoate), and combinations thereof.

20. The composition of claim 18 wherein the adjuvant is selected from the group of
a saponin associated with a metallic salt,
3D-MPL, QS21 and a CpG oligonucleotide,
saponin in the form of a liposome, and
an ISCOM.

21. The composition of claim 17, which further comprises one or more further antigens from *P. falciparium* and/or *P. vivax* in admixture.

22. The composition of claim 17, which further comprises a surfactant.

23. A method of inducing an immune response to *Plasmodium vivax* in a patient susceptible to *Plasmodium vivax* infection comprising administering to the patient an effective amount of the immunogenic hybrid fusion protein as claimed in claim 1.

24. The composition of claim 11, wherein the adjuvant comprises QS21 and 3D-MPL.

25. The composition of claim 11, wherein the adjuvant comprises QS21 and 3D-MPL in a liposomal formulation.

26. A kit comprising the hybrid fusion protein of claim 1.

27. The immunogenic hybrid fusion protein of claim 1, further comprising one or more *P. vivax* type I circumsporozoite (CS) protein monomer sequences of SEQ ID NO: 4.

\* \* \* \* \*

SEQUENCE LISTING

```
<160> NUMBER OF SEQ ID NOS: 30

<210> SEQ ID NO 1
<211> LENGTH: 5
<212> TYPE: PRT
<213> ORGANISM: Plasmodium Vivax

<400> SEQUENCE: 1

Lys Leu Lys Gln Pro
1               5

<210> SEQ ID NO 2
<211> LENGTH: 6
<212> TYPE: PRT
<213> ORGANISM: Plasmodium Vivax

<400> SEQUENCE: 2

Cys Ser Val Thr Cys Gly
1               5

<210> SEQ ID NO 3
<211> LENGTH: 9
<212> TYPE: PRT
<213> ORGANISM: Plasmodium Vivax

<400> SEQUENCE: 3

Gly Asp Arg Ala Ala Gly Gln Pro Ala
1               5

<210> SEQ ID NO 4
<211> LENGTH: 9
<212> TYPE: PRT
<213> ORGANISM: Plasmodium Vivax

<400> SEQUENCE: 4

Gly Asp Arg Ala Asp Gly Gln Pro Ala
1               5

<210> SEQ ID NO 5
<211> LENGTH: 9
<212> TYPE: PRT
```

```
<213> ORGANISM: Plasmodium Vivax

<400> SEQUENCE: 5

Gly Asp Arg Ala Asp Gly Gln Ala Ala
 1               5

<210> SEQ ID NO 6
<211> LENGTH: 9
<212> TYPE: PRT
<213> ORGANISM: Plasmodium Vivax

<400> SEQUENCE: 6

Gly Asn Gly Ala Gly Gly Gln Pro Ala
 1               5

<210> SEQ ID NO 7
<211> LENGTH: 9
<212> TYPE: PRT
<213> ORGANISM: Plasmodium Vivax

<400> SEQUENCE: 7

Gly Asp Gly Ala Ala Gly Gln Pro Ala
 1               5

<210> SEQ ID NO 8
<211> LENGTH: 9
<212> TYPE: PRT
<213> ORGANISM: Plasmodium Vivax

<400> SEQUENCE: 8

Gly Asp Arg Ala Ala Gly Gln Ala Ala
 1               5

<210> SEQ ID NO 9
<211> LENGTH: 9
<212> TYPE: PRT
<213> ORGANISM: Plasmodium Vivax

<400> SEQUENCE: 9

Gly Asn Gly Ala Gly Gly Gln Ala Ala
 1               5

<210> SEQ ID NO 10
<211> LENGTH: 9
<212> TYPE: PRT
<213> ORGANISM: Plasmodium Vivax

<400> SEQUENCE: 10

Ala Asn Gly Ala Gly Asn Gln Pro Gly
 1               5

<210> SEQ ID NO 11
<211> LENGTH: 12
<212> TYPE: PRT
<213> ORGANISM: Plasmodium Vivax

<400> SEQUENCE: 11

Gly Gly Asn Ala Ala Asn Lys Lys Ala Glu Asp Ala
 1               5                  10

<210> SEQ ID NO 12
<211> LENGTH: 771
<212> TYPE: DNA
<213> ORGANISM: Artificial Sequence
<220> FEATURE:
```

<223> OTHER INFORMATION: Nucleotide sequence for a hybrid
      circumsporozite protein (codon optimized for expression in E.
      coli)

<400> SEQUENCE: 12

```
acacattgcg gacataatgt agatttatct aaagctataa atttaaatgg tgtaaacttc    60
aataacgtag acgctagttc actcggggct gcgcacgtag gtcagtctgc tagcagggggg   120
cgcggtctcg gggaaaaccc agacgacgaa gaaggtgatg ctaaaaagaa aaaggacggt   180
aaaaaagcgg aaccaaaaaa tccaagggaa aataaattaa acagcccggg gatcgcgcg    240
gatggtcaag cggcgggtaa tggggcgggg ggtcaaccag cggggatcg cgcggctggt   300
cagccagcgg gggatcgcgc ggctggtcag ccagcggggg atggtgcggc tggccaacca   360
gcggggatc gcgcggatgg tcagccagcg gggatcgcg cggatggtca accagccggt    420
gatcgcgcgg ctggccaagc ggccggtaat ggggcgggg gtcaagcggc cgcgaacgga   480
gcggggaacc agccaggcgg cggtaacgct gcgaataaaa aagcggaaga tgcgggtggt   540
aacgcgggcg gtaatgcggg cggccaaggt cagaacaacg aaggggctaa tgcaccaaac   600
gaaaaatctg tcaaagaata tctcgataaa gtccgcgcta cagtagggac agaatggacg   660
ccatgctctg taacatgtgg tgtcggggta cgcgtgcgcc gccgtgtcaa tgcggctaac   720
aaaaaaccag aagatctcac gttaaatgat ctcgaaacgg atgtctgcac a           771
```

<210> SEQ ID NO 13
<211> LENGTH: 257
<212> TYPE: PRT
<213> ORGANISM: Artificial Sequence
<220> FEATURE:
<223> OTHER INFORMATION: Amino acid sequence for a hybrid
      circumsporozite protein derived from different types of Plasmodium
      Vivax

<400> SEQUENCE: 13

```
Thr His Cys Gly His Asn Val Asp Leu Ser Lys Ala Ile Asn Leu Asn
 1               5                  10                  15

Gly Val Asn Phe Asn Asn Val Asp Ala Ser Ser Leu Gly Ala Ala His
            20                  25                  30

Val Gly Gln Ser Ala Ser Arg Gly Arg Gly Leu Gly Glu Asn Pro Asp
        35                  40                  45

Asp Glu Glu Gly Asp Ala Lys Lys Lys Asp Gly Lys Lys Ala Glu
    50                  55                  60

Pro Lys Asn Pro Arg Glu Asn Lys Leu Lys Gln Pro Gly Asp Arg Ala
 65                  70                  75                  80

Asp Gly Gln Ala Ala Gly Asn Gly Ala Gly Gly Gln Pro Ala Gly Asp
                85                  90                  95

Arg Ala Ala Gly Gln Pro Ala Gly Asp Arg Ala Ala Gly Gln Pro Ala
            100                 105                 110

Gly Asp Gly Ala Ala Gly Gln Pro Ala Gly Asp Arg Ala Asp Gly Gln
        115                 120                 125

Pro Ala Gly Asp Arg Ala Asp Gly Gln Pro Ala Gly Asp Arg Ala Ala
    130                 135                 140

Gly Gln Ala Ala Gly Asn Gly Ala Gly Gly Gln Ala Ala Ala Asn Gly
145                 150                 155                 160

Ala Gly Asn Gln Pro Gly Gly Gly Asn Ala Ala Asn Lys Lys Ala Glu
                165                 170                 175

Asp Ala Gly Gly Asn Ala Gly Gly Asn Ala Gly Gly Gln Gly Gln Asn
            180                 185                 190
```

Asn Glu Gly Ala Asn Ala Pro Asn Glu Lys Ser Val Lys Glu Tyr Leu
          195                 200                 205

Asp Lys Val Arg Ala Thr Val Gly Thr Glu Trp Thr Pro Cys Ser Val
      210                 215                 220

Thr Cys Gly Val Gly Val Arg Val Arg Arg Val Asn Ala Ala Asn
225                 230                 235                 240

Lys Lys Pro Glu Asp Leu Thr Leu Asn Asp Leu Glu Thr Asp Val Cys
              245                 250                 255

Thr

<210> SEQ ID NO 14
<211> LENGTH: 9
<212> TYPE: PRT
<213> ORGANISM: Plasmodium Vivax

<400> SEQUENCE: 14

Ala Asn Gly Ala Gly Asp Gln Pro Gly
 1               5

<210> SEQ ID NO 15
<211> LENGTH: 771
<212> TYPE: DNA
<213> ORGANISM: Artificial Sequence
<220> FEATURE:
<223> OTHER INFORMATION: Nucleotide sequence for a hybrid
      circumsporozite protein derived from different types of Plasmodium
      Vivax (codon optimized for expression in yeast)

<400> SEQUENCE: 15
acccattgtg gtcacaatgt cgatttgtct aaggccatta acttgaacgg tgttaatttc      60
aacaacgtcg atgcttcttc tttaggtgcc gctcatgttg tcaatctgc ttcaagaggt     120 agaggtttag gtgaaaaccc agacgacgaa gaaggtgacg ctaagaagaa gaaggacggt     180
aagaaggccg aaccaaagaa cccaagagaa acaagttga acaaccagg tgacagagcc      240 gacggacaag cagctggtaa tggtgctgga ggtcaaccag ctggtgacag agctgccggt     300
cagcctgctg gtgatagagc tgctggacaa cctgctggag acggtgccgc cggtcaacct     360
gctggtgata gagcagacgg acaaccagct ggtgaccgtg ctgacggaca gccagccggc     420
gatagggctg caggtcaagc cgctggtaac ggtgccggtg gtcaagctgc tgctaacggt     480
gctggtaacc aaccaggtgg tgtaacgct gccaacaaga aagctgaaga cgctggtggt      540
aatgctggag gtaatgcagg tggtcagggt caaacaacg aaggtgctaa cgctccaaac      600
gaaaagtctg ttaaggaata cttagataag gttagagcta ctgtcggtac tgaatggact     660
ccatgttctg ttacttgtgg tgtcggtgtt agagttagaa gaagagttaa cgccgctaac     720
aagaagccag aagacttgac tctaaacgac ttggaaactg acgtttgtac t              771

<210> SEQ ID NO 16
<211> LENGTH: 1485
<212> TYPE: DNA
<213> ORGANISM: Artificial Sequence
<220> FEATURE:
<223> OTHER INFORMATION: Nucleotide sequence for a hybrid fusion protein
      (CSV-S) of circumsporozite protein derived from
      different types of Plasmodium Vivax and the S
      antigen from Hepatitis B

<400> SEQUENCE: 16
atgatggctc ccgggaccca ttgtggtcac aatgtcgatt tgtctaaggc cattaacttg      60

```
aacggtgtta atttcaacaa cgtcgatgct tcttctttag gtgccgctca tgttggtcaa      120
tctgcttcaa gaggtagagg tttaggtgaa aacccagacg acgaagaagg tgacgctaag      180
aagaagaagg acggtaagaa ggccgaacca aagaacccaa gagaaaacaa gttgaaacaa      240
ccaggtgaca gagccgacgg acaagcagct ggtaatggtg ctggaggtca accagctggt      300
gacagagctg ccggtcagcc tgctggtgat agagctgctg acaacctgc tggagacggt       360 gccgccggtc aacctgctgg tgatagagca cgacagcaac cagctggtga ccgtgctgac      420
ggacagccag ccggcgatag ggctgcaggt caagccgctg gtaacggtgc cggtggtcaa      480
gctgctgcta cggtgctgg taaccaacca ggtggtggta cgctgccaa caagaaagct        540 gaagacgctg gtggtaatgc tggaggtaat gcaggtggtc agggtcaaaa aacgaaggt      600 gctaacgctc caaacgaaaa gtctgttaag gaatacttag ataaggttag agctactgtc      660
ggtactgaat ggactccatg ttctgttact tgtggtgtcg gtgttagagt tagaagaaga      720
gttaacgccg ctaacaagaa gccagaagac ttgactctaa acgacttgga aactgacgtt      780
tgtactcccg ggcctgtgac gaacatggag aacatcacat caggattcct aggacccctg      840
ctcgtgttac aggcggggtt tttcttgttg acaagaatcc tcacaatacc gcagagtcta      900
gactcgtggt ggacttctct caattttcta ggggatcac ccgtgtgtct tggccaaaat       960
tcgcagtccc caacctccaa tcactcacca acctcctgtc ctccaatttg tcctggttat     1020
cgctggatgt gtctgcggcg ttttatcata ttcctcttca tcctgctgct atgcctcatc     1080
ttcttattgg ttcttctgga ttatcaaggt atgttgcccg tttgtcctct aattccagga     1140
tcaacaacaa ccaatacggg accatgcaaa acctgcacga ctcctgctca aggcaactct     1200
atgtttccct catgttgctg tacaaaacct acggatggaa attgcacctg tattcccatc     1260
ccatcgtcct gggctttcgc aaaataccta tgggagtggg cctcagtccg tttctcttgg     1320
ctcagtttac tagtgccatt tgttcagtgg ttcgtagggc tttcccccac tgtttggctt     1380
tcagctatat ggatgatgtg gtattggggg ccaagtctgt acagcatcgt gagtcccttt     1440
ataccgctgt taccaatttt cttttgtctc tgggtataca tttaa                     1485
```

<210> SEQ ID NO 17
<211> LENGTH: 494
<212> TYPE: PRT
<213> ORGANISM: Artificial Sequence
<220> FEATURE:
<223> OTHER INFORMATION: Amino acid sequence for a hybrid fusion protein
      (CSV-S) of circumsporozite protein derived from
      different types of Plasmodium Vivax and the S
      antigen from Hepatitis B

<400> SEQUENCE: 17

```
Met Met Ala Pro Gly Thr His Cys Gly His Asn Val Asp Leu Ser Lys
 1               5                  10                  15

Ala Ile Asn Leu Asn Gly Val Asn Phe Asn Asn Val Asp Ala Ser Ser
                20                  25                  30

Leu Gly Ala Ala His Val Gly Gln Ser Ala Ser Arg Gly Arg Gly Leu
            35                  40                  45

Gly Glu Asn Pro Asp Asp Glu Glu Gly Asp Ala Lys Lys Lys Lys Asp
        50                  55                  60

Gly Lys Lys Ala Glu Pro Lys Asn Pro Arg Glu Asn Lys Leu Lys Gln
 65                  70                  75                  80

Pro Gly Asp Arg Ala Asp Gly Gln Ala Ala Gly Asn Gly Ala Gly Gly
                85                  90                  95
```

Gln Pro Ala Gly Asp Arg Ala Ala Gly Gln Pro Ala Gly Asp Arg Ala
            100                 105                 110

Ala Gly Gln Pro Ala Gly Asp Gly Ala Ala Gly Gln Pro Ala Gly Asp
        115                 120                 125

Arg Ala Asp Gly Gln Pro Ala Gly Asp Arg Ala Asp Gly Gln Pro Ala
    130                 135                 140

Gly Asp Arg Ala Ala Gly Gln Ala Ala Gly Asn Gly Ala Gly Gly Gln
145                 150                 155                 160

Ala Ala Ala Asn Gly Ala Gly Asn Gln Pro Gly Gly Asn Ala Ala
                165                 170                 175

Asn Lys Lys Ala Glu Asp Ala Gly Asn Ala Gly Asn Ala Gly
                180                 185                 190

Gly Gln Gly Gln Asn Asn Glu Gly Ala Asn Ala Pro Asn Glu Lys Ser
        195                 200                 205

Val Lys Glu Tyr Leu Asp Lys Val Arg Ala Thr Val Gly Thr Glu Trp
    210                 215                 220

Thr Pro Cys Ser Val Thr Cys Gly Val Gly Val Arg Val Arg Arg
225                 230                 235                 240

Val Asn Ala Ala Asn Lys Lys Pro Glu Asp Leu Thr Leu Asn Asp Leu
                245                 250                 255

Glu Thr Asp Val Cys Thr Pro Gly Pro Val Thr Asn Met Glu Asn Ile
            260                 265                 270

Thr Ser Gly Phe Leu Gly Pro Leu Val Leu Gln Ala Gly Phe Phe
        275                 280                 285

Leu Leu Thr Arg Ile Leu Thr Ile Pro Gln Ser Leu Asp Ser Trp Trp
    290                 295                 300

Thr Ser Leu Asn Phe Leu Gly Gly Ser Pro Val Cys Leu Gly Gln Asn
305                 310                 315                 320

Ser Gln Ser Pro Thr Ser Asn His Ser Pro Thr Ser Cys Pro Pro Ile
                325                 330                 335

Cys Pro Gly Tyr Arg Trp Met Cys Leu Arg Arg Phe Ile Ile Phe Leu
            340                 345                 350

Phe Ile Leu Leu Leu Cys Leu Ile Phe Leu Leu Val Leu Leu Asp Tyr
        355                 360                 365

Gln Gly Met Leu Pro Val Cys Pro Leu Ile Pro Gly Ser Thr Thr Thr
    370                 375                 380

Asn Thr Gly Pro Cys Lys Thr Cys Thr Thr Pro Ala Gln Gly Asn Ser
385                 390                 395                 400

Met Phe Pro Ser Cys Cys Thr Lys Pro Thr Asp Gly Asn Cys Thr
                405                 410                 415

Cys Ile Pro Ile Pro Ser Ser Trp Ala Phe Ala Lys Tyr Leu Trp Glu
            420                 425                 430

Trp Ala Ser Val Arg Phe Ser Trp Leu Ser Leu Val Pro Phe Val
        435                 440                 445

Gln Trp Phe Val Gly Leu Ser Pro Thr Val Trp Leu Ser Ala Ile Trp
    450                 455                 460

Met Met Trp Tyr Trp Gly Pro Ser Leu Tyr Ser Ile Val Ser Pro Phe
465                 470                 475                 480

Ile Pro Leu Leu Pro Ile Phe Phe Cys Leu Trp Val Tyr Ile
                485                 490

<210> SEQ ID NO 18
<211> LENGTH: 3509
<212> TYPE: DNA

-continued

<213> ORGANISM: Artificial Sequence
<220> FEATURE:
<223> OTHER INFORMATION: Nucleotide sequence for a hybrid fusion protein (RTS) of circumsporozite protein of Plasmodium Falciparum and the S antigen from Hepatitis B

<400> SEQUENCE: 18

```
aagcttacca gttctcacac ggaacaccac taatggacac aaattcgaaa tactttgacc 60
ctattttcga ggaccttgtc accttgagcc caagagagcc aagatttaaa ttttcctatg 120
acttgatgca aattcccaaa gctaataaca tgcaagacac gtacggtcaa gaagacatat 180
ttgacctctt aactggttca gacgcgactg cctcatcagt aagacccgtt gaaaagaact 240
tacctgaaaa aaacgaatat atactagcgt tgaatgttag cgtcaacaac aagaagttta 300
atgacgcgga ggccaaggca aaaagattcc ttgattacgt aagggagtta gaatcatttt 360
gaataaaaaa cacgcttttt cagttcgagt ttatcattat caatactgcc atttcaaaga 420
atacgtaaat aattaatagt agtgattttc ctaactttat ttagtcaaaa attagccttt 480
taattctgct gtaacccgta catgcccaaa atagggggcg ggttacacag aatatataac 540
atcgtaggtg tctgggtgaa cagtttatcc ctggcatcca ctaaatataa tggagctcgc 600
ttttaagctg gcatccagaa aaaaaaagaa tcccagcacc aaaatattgt tttcttcacc 660
aaccatcagt tcataggtcc attctcttag cgcaactaca gagaacaggg gcacaaacag 720
gcaaaaaacg ggcacaacct caatggagtg atgcaacctg cctggagtaa atgatgacac 780
aaggcaattg acccacgcat gtatctatct cattttctta caccttctat taccttctgc 840
tctctctgat ttggaaaaag ctgaaaaaaa aggttgaaac cagttccctg aaattattcc 900
cctacttgac taataagtat ataaagacgg taggtattga ttgtaattct gtaaatctgt 960
aaatctattt cttaaacttc ttaaattcta cttttatagt tagtcttttt tttagtttta 1020
aaacaccaag aacttagttt cgaataaaca cacataaaca aacaaaatga tggctcccga 1080
tcctaatgca aatccaaatg caaacccaaa tgcaaaccca aacgcaaacc ccaatgcaaa 1140
tcctaatgca aaccccaatg caaatcctaa tgcaaatcct aatgccaatc caaatgcaaa 1200
tccaaatgca aacccaaacg caaaccccaa tgcaaatcct aatgccaatc caaatgcaaa 1260
tccaaatgca aacccaaatg caaacccaaa tgcaaacccc aatgcaaatc ctaataaaaa 1320
caatcaaggt aatggacaag gtcacaatat gccaaatgac ccaaaccgaa atgtagatga 1380
aaatgctaat gccaacaatg ctgtaaaaaa taataataac gaagaaccaa gtgataagca 1440
catagaacaa tatttaaaga aaataaaaaa ttctatttca actgaatggt ccccatgtag 1500
tgtaacttgt ggaaatggta ttcaagttag aataaagcct ggctctgcta ataaacctaa 1560
agacgaatta gattatgaaa atgatattga aaaaaaaatt tgtaaaatgg aaaagtgctc 1620
gagtgtgttt aatgtcgtaa atagtcgacc tgtgacgaac atggagaaca tcacatcagg 1680
attcctagga cccctgctcg tgttacaggc ggggtttttc ttgttgacaa gaatcctcac 1740
aataccgcag agtctagact cgtggtggac ttctctcaat tttctagggg gatcacccgt 1800
gtgtcttggc caaaattcgc agtccccaac ctccaatcac tcaccaacct cctgtcctcc 1860
aatttgtcct ggttatcgct ggatgtgtct gcgcgtttta tcatattcct cttcatcctg 1920
ctgctatgcc tcatcttctt attggttctt ctggattatc aaggtatgtt gcccgtttgt 1980
cctctaattc caggatcaac aacaaccaat acgggaccat gcaaaacctg cacgactcct 2040
gctcaaggca actctatgtt tccctcatgt tgctgtacaa aacctacgga tggaaattgc 2100
acctgtattc ccatcccatc gtcctgggct ttcgcaaaat acctatggga gtgggcctca 2160

```
gtccgtttct cttggctcag tttactagtg ccatttgttc agtggttcgt agggctttcc    2220
cccactgttt ggctttcagc tatatggatg atgtggtatt gggggccaag tctgtacagc    2280
atcgtgagtc cctttatacc gctgttacca attttctttt gtctctgggt atacatttaa    2340
cgaattccaa gctgaaacaa ttcaaaggtt ttcaaatcaa tcaagaactt gtctctgtgg    2400
ctgatccaaa ctacaaattt atgcattgtc tgccaagaca tcaagaagaa gttagtgatg    2460
atgtctttta tggagagcat tccatagtct ttgaagaagc agaaaacaga ttatatgcag    2520
ctatgtctgc cattgatatc tttgttaata ataaaggtaa tttcaaggac ttgaaataat    2580
ccttctttcg tgttcttaat aactaatata taaatacaga tatagatgca tgaataatga    2640
tatacattga ttattttgca atgtcaatta aaaaaaaaaa atgttagtaa aactatgtta    2700
cattccaagc aaataaagca cttggttaaa cgaaattaac gttttttaaga cagccagacc    2760 gcggtctaaa aatttaaata tacactgcca acaaattcct tcgagttgtc caatttcacc    2820
acttttatat tttcatcaac ttcagcagat tcaaccttct cacatagaac attggaataa    2880
acagccttaa caccactttc aagtttgcac agcgtaatat gaggaatttt gttttgacaa    2940
cacaaccctt taattttctc attgttttca tcaattatgc atccatcttt atctttagac    3000
agttccacta caatagcaat agttttttca tcccaacata gttttttcgag cctaaaattc    3060 agttgtcgg tcgttttacc tgcgtatttt ggttattacc agagccttgt gcattttcta    3120
tgcggttgtt attgtactcc gttatctggt cagtgtatct gttacaatat gattccacaa    3180
cttttttgcc tctttttcac gggacgacat gacatgacct aatgttatat gaagttcctt    3240
ctgaactttt ccactagcta gtaaatgctt gaatttctca gtcagctctg catcgctagc    3300
aatacacctc ttgaccaatc aataatttca tcgtagtttt ctatttagct gagatatatg    3360
taggtttaat taacttagcg ttttttgttg attattgttg cctttaccaa ctattttttct    3420 cacagtaggt ttgtaatcta agctccttct gaacgctgtc tcaatttcat catctttcgg    3480
gatctctggt accaaaattg gataagctt                                       3509
```

<210> SEQ ID NO 19
<211> LENGTH: 1485
<212> TYPE: DNA
<213> ORGANISM: Artificial Sequence
<220> FEATURE:
<223> OTHER INFORMATION: Hybrid gene encoding fusion protein of
    Circumsporozite Protein derived from Plasomodium
    Vivax and S antigen from Hepatitis B cloned into
    pHIL-D2

<400> SEQUENCE: 19

```
atggttgctc ccgggaccca ttgtggtcac aatgtcgatt tgtctaaggc cattaacttg      60
aacggtgtta atttcaacaa cgtcgatgct tcttctttag gtgccgctca tgttggtcaa     120
tctgcttcaa gaggtagagg tttaggtgaa aacccagacg acgaagaagg tgacgctaag     180
aagaagaagg acgtaagaa ggccgaacca agaacccaa gagaaacaa gttgaaacaa      240 ccaggtgaca gagccgacgg acaagcagct ggtaatggtg ctggaggtca accagctggt     300
gacagagctg ccggtcagcc tgctggtgat agagctgctg acaacctgc tggagacggt     360 gccgccggtc aacctgctgg tgatagagca gacggacaac cagctggtga ccgtgctgac     420
ggacagccag ccggcgatag ggctgcaggt caagccgctg gtaacggtgc cggtggtcaa     480
gctgctgcta acggtgctgg taaccaacca ggtggtggta acgctgccaa caagaaagct     540
gaagacgctg gtggtaatgc tggaggtaat gcaggtggtc agggtcaaaa caacgaaggt     600
```

```
gctaacgctc caaacgaaaa gtctgttaag gaatacttag ataaggttag agctactgtc    660
ggtactgaat ggactccatg ttctgttact tgtggtgtcg gtgttagagt tagaagaaga    720
gttaacgccg ctaacaagaa gccagaagac ttgactctaa acgacttgga aactgacgtt    780
tgtactcccg ggcctgtgac gaacatggag aacatcacat caggattcct aggacccctg    840
ctcgtgttac aggcggggtt tttcttgttg acaagaatcc tcacaatacc gcagagtcta    900
gactcgtggt ggacttctct caattttcta gggggatcac ccgtgtgtct ggccaaaat    960 tcgcagtccc caacctccaa tcactcacca acctcctgtc ctccaatttg tcctggttat   1020
cgctggatgt gtctgcggcg ttttatcata ttcctcttca tcctgctgct atgcctcatc   1080
ttcttattgg ttcttctgga ttatcaaggt atgttgcccg tttgtcctct aattccagga   1140
tcaacaacaa ccaatacggg accatgcaaa acctgcacga ctcctgctca aggcaactct   1200
atgtttccct catgttgctg tacaaaacct acggatggaa attgcacctg tattcccatc   1260
ccatcgtcct gggcttttcgc aaaataccta tgggagtggg cctcagtccg tttctcttgg   1320
ctcagtttac tagtgccatt tgttcagtgg ttcgtagggc ttttcccccac tgtttggctt   1380 tcagctatat ggatgatgtg gtattggggg ccaagtctgt acagcatcgt gagtcccttt   1440
ataccgctgt taccaatttt cttttgtctc tgggtataca tttaa                   1485
```

<210> SEQ ID NO 20
<211> LENGTH: 494
<212> TYPE: PRT
<213> ORGANISM: Artificial Sequence
<220> FEATURE:
<223> OTHER INFORMATION: Hybrid fusion protein of Circumsporozite
  Protein derived from Plasomodium Vivax and S antigen from
  Hepatitis B as expressed by Pichia Pastoris

<400> SEQUENCE: 20

```
Met Val Ala Pro Gly Thr His Cys Gly His Asn Val Asp Leu Ser Lys
  1               5                  10                  15

Ala Ile Asn Leu Asn Gly Val Asn Phe Asn Asn Val Asp Ala Ser Ser
             20                  25                  30

Leu Gly Ala Ala His Val Gly Gln Ser Ala Ser Arg Gly Arg Gly Leu
         35                  40                  45

Gly Glu Asn Pro Asp Asp Glu Glu Gly Asp Ala Lys Lys Lys Lys Asp
     50                  55                  60

Gly Lys Lys Ala Glu Pro Lys Asn Pro Arg Glu Asn Lys Leu Lys Gln
 65                  70                  75                  80

Pro Gly Asp Arg Ala Asp Gly Gln Ala Ala Gly Asn Gly Ala Gly Gly
                 85                  90                  95

Gln Pro Ala Gly Asp Arg Ala Gly Gln Pro Ala Gly Asp Arg Ala
            100                 105                 110

Ala Gly Gln Pro Ala Gly Asp Gly Ala Ala Gly Gln Pro Ala Gly Asp
        115                 120                 125

Arg Ala Asp Gly Gln Pro Ala Gly Asp Arg Ala Asp Gly Gln Pro Ala
    130                 135                 140

Gly Asp Arg Ala Ala Gly Gln Ala Ala Gly Asn Gly Ala Gly Gly Gln
145                 150                 155                 160

Ala Ala Ala Asn Gly Ala Gly Asn Gln Pro Gly Gly Asn Ala Ala
                165                 170                 175

Asn Lys Lys Ala Glu Asp Ala Gly Gly Asn Ala Gly Gly Asn Ala Gly
            180                 185                 190
```

```
Gly Gln Gly Gln Asn Asn Glu Gly Ala Asn Ala Pro Asn Glu Lys Ser
            195

-continued

```
                 50                  55                  60
Pro Asn Ala Asn Pro Asn Leu Asn Pro Asn Ala Asn Pro Asn Ala Asn
 65                  70                  75                  80

Pro Asn Ala Asn Pro Asn Lys Asn Asn Gln Gly Leu Asn Gly Gln Gly
                 85                  90                  95

His Asn Met Pro Asn Asp Pro Asn Asp Pro Asn Arg Asn Val Asp Glu
                100                 105                 110

Asn Ala Asn Ala Asn Asn Ala Val Lys Asn Asn Asn Glu Glu Pro
                115                 120                 125

Ser Asp Lys His Ile Glu Gly Leu Tyr Leu Lys Lys Ile Lys Asn Ser
130                 135                 140

Ile Ser Thr Glu Trp Ser Pro Cys Ser Val Thr Cys Tyr Gly Asn Gly
145                 150                 155                 160

Ile Gln Val Arg Ile Lys Pro Gly Ser Ala Asn Lys Pro Lys Asp Glu
                165                 170                 175

Leu Asp Tyr Glu Asn Asp Ile Glu Lys Lys Ile Cys Lys Met Glu Lys
                180                 185                 190

Cys Ser Ser Val Pro His Asn Val Val Asn Ser Arg Pro Val Thr Asn
                195                 200                 205

Met Glu Asn Ile Thr Ser Gly Phe Leu Gly Leu Pro Leu Leu Val Leu
                210                 215                 220

Gln Ala Gly Phe Phe Leu Leu Thr Arg Ile Leu Thr Ile Pro Gly Leu
225                 230                 235                 240

Ser Leu Asp Ser Trp Trp Thr Ser Leu Asn Phe Leu Gly Gly Ser Pro
                245                 250                 255

Val Cys Leu Gly Leu Gln Asn Ser Gln Ser Pro Thr Ser Asn His Ser
                260                 265                 270

Pro Thr Ser Cys Pro Pro Ile Cys Pro Arg Gly Tyr Arg Trp Met Cys
                275                 280                 285

Leu Arg Arg Phe Ile Ile Phe Leu Phe Ile Leu Leu Leu Cys Tyr Leu
                290                 295                 300

Ile Phe Leu Leu Val Leu Leu Asp Tyr Gln Gly Met Leu Pro Val Cys
305                 310                 315                 320

Pro Leu Ile Leu Pro Gly Ser Thr Thr Thr Asn Thr Gly Pro Cys Lys
                325                 330                 335

Thr Cys Thr Thr Pro Ala Gln Gly Leu Asn Ser Met Phe Pro Ser Cys
                340                 345                 350

Cys Cys Thr Lys Pro Thr Asp Gly Asn Cys Thr Cys Ile Leu Pro Ile
                355                 360                 365

Pro Ser Ser Trp Ala Phe Ala Lys Thr Leu Trp Glu Trp Ala Ser Val
                370                 375                 380

Arg Pro His Ser Trp Leu Ser Leu Leu Val Pro Phe Val Gln Trp Phe
385                 390                 395                 400

Val Gly Leu Ser Pro Thr Val Ala Trp Leu Ser Ala Ile Trp Met Met
                405                 410                 415

Trp Tyr Trp Gly Pro Ser Leu Tyr Ser Ile Val Ser Glu Pro Phe Ile
                420                 425                 430

Pro Leu Leu Pro Ile Phe Phe Cys Leu Trp Val Tyr Ile
                435                 440                 445

<210> SEQ ID NO 22
<211> LENGTH: 42
<212> TYPE: DNA
<213> ORGANISM: Unknown
```

```
<220> FEATURE:
<223> OTHER INFORMATION: Information relating to cloning site of plasmid
      pGF1-S2 shown in Figure 4

<400> SEQUENCE: 22
atgatggctc ccgggatcct acccgggcct gtgacgaaga tg                    42

<210> SEQ ID NO 23
<211> LENGTH: 10
<212> TYPE: PRT
<213> ORGANISM: Unknown
<220> FEATURE:
<223> OTHER INFORMATION: Information relating to cloning site of plasmid
      pGF1-S2 shown in Figure 4

<400> SEQUENCE: 23

Met Met Ala Pro Gly Pro Val Thr Asn Met
1               5                   10

<210> SEQ ID NO 24
<211> LENGTH: 20
<212> TYPE: DNA
<213> ORGANISM: Human

<400> SEQUENCE: 24
tccatgacgt tcctgacgtt                                             20

<210> SEQ ID NO 25
<211> LENGTH: 18
<212> TYPE: DNA
<213> ORGANISM: Human

<400> SEQUENCE: 25
tctcccagcg tgcgccat                                               18

<210> SEQ ID NO 26
<211> LENGTH: 30
<212> TYPE: DNA
<213> ORGANISM: Human

<400> SEQUENCE: 26
accgatgacg tcgccggtga cggcaccacg                                  30

<210> SEQ ID NO 27
<211> LENGTH: 24
<212> TYPE: DNA
<213> ORGANISM: Human

<400> SEQUENCE: 27
tcgtcgtttt gtcgttttgt cgtt                                        24

<210> SEQ ID NO 28
<211> LENGTH: 20
<212> TYPE: DNA
<213> ORGANISM: Human

<400> SEQUENCE: 28
tccatgacgt tcctgatgct                                             20

<210> SEQ ID NO 29
<211> LENGTH: 22
<212> TYPE: DNA
<213> ORGANISM: Human

<400> SEQUENCE: 29
```

```
tcgacgtttt cggcgcgcgc cg                                             22
```

<210> SEQ ID NO 30
<211> LENGTH: 430
<212> TYPE: PRT
<213> ORGANISM: Artificial Sequence
<220> FEATURE:
<223> OTHER INFORMATION: Amino acid sequence for a hybrid fusion protein
      (RTS) of circumsporozite protein of Plasmodium
      Falciparum and the S antigen from Hepatitis B

<400> SEQUENCE: 30

```
Met Met Ala Pro Ala Glu Pro Lys Asn Pro Arg Glu Asn Lys Leu Lys
 1               5                  10                  15

Gln Pro Gly Asp Arg Ala Asp Gly Gln Ala Ala Gly Asn Gly Ala Gly
            20                  25                  30

Gly Gln Pro Ala Gly Asp Arg Ala Ala Gly Gln Pro Ala Gly Asp Arg
        35                  40                  45

Ala Ala Gly Gln Pro Ala Gly Asp Gly Ala Ala Gly Gln Pro Ala Gly
    50                  55                  60

Asp Arg Ala Asp Gly Gln Pro Ala Gly Asp Arg Ala Asp Gly Gln Pro
65                  70                  75                  80

Ala Gly Asp Arg Ala Ala Gly Gln Ala Ala Gly Asn Gly Ala Gly Gly
                85                  90                  95

Gln Ala Ala Asn Gly Ala Gly Asn Gln Pro Gly Gly Asn Ala
            100                 105                 110

Ala Asn Lys Lys Ala Glu Asp Ala Gly Gly Asn Ala Gly Gly Asn Ala
            115                 120                 125

Gly Gly Gln Gly Gln Asn Asn Glu Gly Ala Asn Ala Pro Asn Glu Lys
        130                 135                 140

Ser Val Lys Glu Tyr Leu Asp Lys Val Arg Ala Thr Val Gly Thr Glu
145                 150                 155                 160

Trp Thr Pro Cys Ser Val Thr Cys Gly Val Gly Val Arg Val Arg Arg
                165                 170                 175

Arg Val Asn Ala Ala Asn Lys Lys Pro Glu Asp Leu Thr Leu Asn Asp
            180                 185                 190

Leu Glu Thr Asp Val Cys Thr Gly Pro Val Thr Asn Met Glu Asn Ile
        195                 200                 205

Thr Ser Gly Phe Leu Gly Pro Leu Leu Val Leu Gln Ala Gly Phe Phe
    210                 215                 220

Leu Leu Thr Arg Ile Leu Thr Ile Pro Gln Ser Leu Asp Ser Trp Trp
225                 230                 235                 240

Thr Ser Leu Asn Phe Leu Gly Gly Ser Pro Val Cys Leu Gly Gln Asn
                245                 250                 255

Ser Gln Ser Pro Thr Ser Asn His Ser Pro Thr Ser Cys Pro Pro Ile
            260                 265                 270

Cys Pro Gly Tyr Arg Trp Met Cys Leu Arg Arg Phe Ile Ile Phe Leu
        275                 280                 285

Phe Ile Leu Leu Leu Cys Leu Ile Phe Leu Leu Val Leu Leu Asp Tyr
    290                 295                 300

Gln Gly Met Leu Pro Val Cys Pro Leu Ile Pro Gly Ser Thr Thr Thr
305                 310                 315                 320

Asn Thr Gly Pro Cys Lys Thr Cys Thr Thr Pro Ala Gln Gly Asn Ser
                325                 330                 335

Met Phe Pro Ser Cys Cys Cys Thr Lys Pro Thr Asp Gly Asn Cys Thr
```

-continued

```
              340                 345                 350
Cys Ile Pro Ile Pro Ser Ser Trp Ala Phe Ala Lys Tyr Leu Trp Glu
            355                 360                 365

Trp Ala Ser Val Arg Phe Ser Trp Leu Ser Leu Leu Val Pro Phe Val
        370                 375                 380

Gln Trp Phe Val Gly Leu Ser Pro Thr Val Trp Leu Ser Ala Ile Trp
385                 390                 395                 400

Met Met Trp Tyr Trp Gly Pro Ser Leu Tyr Ser Ile Val Ser Pro Phe
                405                 410                 415

Ile Pro Leu Leu Pro Ile Phe Phe Cys Leu Trp Val Tyr Ile
            420                 425                 430
```